United States Patent
Molina et al.

(10) Patent No.: US 11,612,713 B2
(45) Date of Patent: Mar. 28, 2023

(54) ENHANCING DEEP SLEEP BASED ON INFORMATION FROM FRONTAL BRAIN ACTIVITY MONITORING SENSORS

(71) Applicant: KONINKLIJKE PHILIPS N.V., Eindhoven (NL)

(72) Inventors: Gary Nelson Garcia Molina, Madison, WI (US); Ulf Grossekathöfer, Eindhoven (NL); Stojan Trajanovski, Eindhoven (NL); Jesse Salazar, Gibsonia, PA (US); Tsvetomira Kirova Tsoneva, Eindhoven (NL); Sander Theodoor Pastoor, Vleuten (NL); Antonio Aquino, Harrison City, PA (US); Adrienne Heinrich, Metro Manila (PH); Birpal Singh Sachdev, Delmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 16/832,509

(22) Filed: Mar. 27, 2020

(65) Prior Publication Data
US 2020/0306494 A1 Oct. 1, 2020

Related U.S. Application Data

(60) Provisional application No. 62/825,088, filed on Mar. 28, 2019.

(51) Int. Cl.
*A61M 21/02* (2006.01)
*A61B 5/00* (2006.01)
(Continued)

(52) U.S. Cl.
CPC ............. *A61M 21/02* (2013.01); *A61B 5/291* (2021.01); *A61B 5/316* (2021.01); *A61B 5/374* (2021.01);
(Continued)

(58) Field of Classification Search
CPC .......... A61M 21/02; A61M 2021/0011; A61M 2021/0027; A61M 2021/0044;
(Continued)

(56) References Cited

U.S. PATENT DOCUMENTS

2006/0293608 A1* 12/2006 Rothman ............... A61M 21/00
368/9
2007/0249952 A1* 10/2007 Rubin ................... A61M 21/00
600/544
(Continued)

FOREIGN PATENT DOCUMENTS

WO WO-2016087983 A1 * 6/2016 ............. A61B 3/113

OTHER PUBLICATIONS

H.-V. V Ngo, A. Miedema, I. Faude, T. Martinetz, M. Molle, and J. Born, "Driving Sleep Slow Oscillations by Auditory Closed-Loop Stimulation—A Self-Limiting Process," J. Neurosci., vol. 35, No. 17, pp. 6630-6638, 2015.
(Continued)

*Primary Examiner* — Sunita Reddy

(57) ABSTRACT

Typically, high NREM stage N3 sleep detection accuracy is achieved using a frontal electrode referenced to an electrode at a distant location on the head (e.g., the mastoid, or the earlobe). For comfort and design considerations it is more convenient to have active and reference electrodes closely positioned on the frontal region of the head. This configuration, however, significantly attenuates the signal, which degrades sleep stage detection (e.g., N3) performance. The present disclosure describes a deep neural network (DNN)
(Continued)

based solution developed to detect sleep using frontal electrodes only. N3 detection is enhanced through post-processing of the soft DNN outputs. Detection of slow-waves and sleep micro-arousals is accomplished using frequency domain thresholds. Volume modulation uses a high-frequency/low-frequency spectral ratio extracted from the frontal signal.

13 Claims, 9 Drawing Sheets

(51) Int. Cl.
  *A61B 5/291* (2021.01)
  *A61B 5/316* (2021.01)
  *A61B 5/374* (2021.01)
  *A61B 5/398* (2021.01)
  *A61M 21/00* (2006.01)

(52) U.S. Cl.
  CPC ............ *A61B 5/398* (2021.01); *A61B 5/4812* (2013.01); *A61B 5/4836* (2013.01); *A61B 5/6803* (2013.01); *A61B 5/7267* (2013.01); *A61B 5/7275* (2013.01); *A61B 2562/0209* (2013.01); *A61M 2021/0011* (2013.01); *A61M 2021/0027* (2013.01); *A61M 2021/0044* (2013.01); *A61M 2021/0055* (2013.01); *A61M 2021/0072* (2013.01); *A61M 2205/50* (2013.01); *A61M 2230/10* (2013.01)

(58) Field of Classification Search
  CPC .. A61M 2021/0055; A61M 2021/0072; A61M 2205/50; A61M 2230/10; A61M 2205/3592; A61M 2205/502; A61M 2230/14; A61B 5/291; A61B 5/316; A61B 5/374; A61B 5/398; A61B 5/4812; A61B 5/4836; A61B 5/6803; A61B 5/7267; A61B 5/7275; A61B 2562/0209; A61B 5/375; A61B 5/7405; A61B 5/742; A61B 5/6814
  USPC .................................................... 600/26–28
  See application file for complete search history.

(56) References Cited

U.S. PATENT DOCUMENTS

| | | | |
|---|---|---|---|
| 2010/0087701 A1* | 4/2010 | Berka | A61M 21/02 600/27 |
| 2011/0295083 A1* | 12/2011 | Doelling | A61B 5/11 600/407 |
| 2016/0082222 A1* | 3/2016 | Garcia Molina | A61B 5/375 600/27 |
| 2016/0302718 A1* | 10/2016 | Laura Lapoint | A61B 5/375 |
| 2017/0215789 A1 | 8/2017 | Mahadevan et al. | |
| 2017/0340854 A1* | 11/2017 | Geerlings | A61B 5/4812 |
| 2018/0311462 A1 | 11/2018 | Garcia | |
| 2019/0282812 A1* | 9/2019 | Simons | A61N 1/20 |

OTHER PUBLICATIONS

M. Bellesi, B. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.
N. A. Papalambros, G. Santostasi, R. G. Malkani, R. Braun, S. Weintraub, K. A. Paller, and P. C. Zee, "Acoustic enhancement of sleep slow oscillations and concomitant memory improvement in older adults," Front. Hum. Neurosci., vol. 11, No. March, pp. 1-14, 2017.
M. M. Leminen, J. Virkkala, E. Saure, T. Paajanen, P. C. Zee, and G. Santostasi, "Enhanced Memory Consolidation via Automatic Sound Stimulation During Non-REM Sleep," Sleep, vol. 40, No. 3, pp. 1-10, 2017.
B. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.
H. H. Jasper, "The ten-twenty electrode system of the international federation," Electroencephalogr. Clin. Neurophysiol., vol. 10, No. 1, pp. 371-375, 1958.
A. Ben-David, "Comparison of classification accuracy using Cohen's Weighted Kappa," Expert Syst. Appl., vol. 34, No. 2, pp. 825-832, Feb. 2008.
U. Zlzer, Digital Audio Effects, pp. 51-52, 2002.
International Search Report and Written Opinion dated Jun. 9, 2020 for International Application No. PCT/EP2020/057711 Filed Mar. 20, 2020.
Garcia-Molina, et at: "Closed-loop system to enhance slow-wave activity", Journal of Neural Engineering, Institute of Physics Publishing, vol. 15, No. 6, Oct. 10, 2018.
Phan, et al: "Joint Classification and Prediction CNN Framework for Automatic Sleep Stage Classification", arniv.org, Cornell University Library, May 17, 2018.

* cited by examiner

ENHANCING DEEP SLEEP BASED ON INFORMATION FROM FRONTAL BRAIN ACTIVITY MONITORING SENSORS

CROSS-REFERENCE TO PRIOR APPLICATIONS

This application claims the benefit of U.S. Provisional Application No. 62/825,088, filed on 28 Mar. 2019. This application is hereby incorporated by reference herein.

BACKGROUND

1. Field

The present disclosure pertains to a system and method for enhancing non-rapid eye movement (NREM) sleep by delivering sensory stimulation to a subject during a sleep session.

2. Description of the Related Art

Systems for monitoring sleep and delivering sensory stimulation to users during sleep are known. Electroencephalogram (EEG) sensor based sleep monitoring and sensory stimulation systems are known. These systems typically control sensory stimulation based on information from a sensor located behind the ear of a user, which can be uncomfortable and/or have other disadvantages. There is a need for a more comfortable system that is still able to monitor sleep and control sensory stimulation to enhance sleep for users.

SUMMARY

It would be advantageous to enhance NREM sleep by delivering sensory stimulation to a subject during a sleep session automatically with a closed loop system based on information from sensors located on the forehead of the subject.

Accordingly, one or more aspects of the present disclosure relate to a system configured to enhance non-rapid eye movement (NREM) sleep by delivering sensory stimulation to a subject during a sleep session. The system comprises first and second sensors, one or more sensory stimulators, one or more hardware processors, and/or other components. The first and second sensors are configured to generate output signals conveying information related to brain activity of the subject during the sleep session. The first and second sensors are configured to engage a forehead of the subject. The one or more sensory stimulators are configured to provide the sensory stimulation to the subject during the sleep session. The one or more hardware processors are coupled to the first and second sensors and the one or more sensory stimulators. The one or more hardware processors are configured by machine-readable instructions. The one or more hardware processors are configured to: detect NREM sleep in the subject during the sleep session based on the output signals from the first and second sensors, and control the one or more sensory stimulators to provide the sensory stimulation to the subject during the NREM sleep to enhance the NREM sleep in the subject during the sleep session.

In some embodiments, the first and second sensors are configured to engage the forehead of the subject at a distance of less than or equal to 10 centimeters from each other. In some embodiments, the first sensor comprises a mid-frontal (FPz) electrooculography (EOG) electrode, and the second sensor comprises a right ocular electrode (EOGR) or a left ocular electrode (EOGL). In some embodiments, either the first sensor or the second sensor is a reference electrode.

In some embodiments, the one or more hardware processors are further configured by machine-readable instructions to obtain historical sleep depth information for a population of users. The historical sleep depth information is related to brain activity of the population of users that indicates sleep depth over time during sleep sessions of the population of users. The one or more hardware processors are configured to cause a neural network to be trained based on the historical sleep depth information by providing the historical sleep depth information as input to the neural network. The one or more hardware processors are configured to cause, based on the output signals from the first and second sensors, the trained neural network to predict future times during the sleep session at which the subject will be in a deep sleep stage. The trained neural network comprises an input layer, an output layer, and one or more intermediate layers between the input layer and the output layer. The one or more hardware processors are configured to determine, with respect to each of the future times, a predicted sleep stage generated by the output layer of the trained neural network, and sleep stage probability values generated by the one or more intermediate layers of the trained neural network. Responsive to (1) the predicted sleep stage being N3, or (2) the predicted sleep stage being N2 with a ratio of a probability of N3 sleep to a probability of N2 sleep being at least 0.5, the one or more hardware processors are configured to cause the one or more sensory stimulators to provide the sensory stimulation to the user at the future times and to modulate a timing and/or intensity of the sensory stimulation during the sleep session based on the one or more probability values generated by the one or more intermediate layers.

In some embodiments, the one or more hardware processors are further configured by machine-readable instructions to detect sleep micro-arousals based on the information in the output signals from the first and second sensors, and control, based on the detected sleep micro-arousals, the one or more sensory stimulators to provide the sensory stimulation to the subject during N3 sleep to enhance the N3 sleep in the subject during the sleep session. A sleep micro-arousal is detected: responsive to a breach of a threshold on a power in a power band of an electroencephalogram (EEG), or based on an additional output from the trained neural network.

In some embodiments, the one or more hardware processors are further configured by machine-readable instructions to detect slow waves based on the information in the output signals from the first and second sensors, and control, based on the detected slow waves, the one or more sensory stimulators to provide the sensory stimulation to the subject during N3 sleep to enhance the N3 sleep in the subject during the sleep session. A slow wave is detected: responsive to a breach of a slow wave minimum peak threshold on a negative going EEG signal, responsive to a breach of a slow wave minimum peak threshold on a filtered negative going EEG signal, wherein the filtering boosts a delta portion of the negative going EEG signal, or based on a comparison of a shape of the filtered negative going EEG signal to a shape of a corresponding slow wave template.

In some embodiments, the one or more hardware processors are further configured by machine-readable instructions: such that the one or more intermediate layers of the trained neural network are configured to generate additional values from two or more corresponding convolutional layers; to determine a ratio of a value from one convolutional layer to a value from another convolutional layer, and to cause the one or more sensory stimulators to modulate the timing and/or intensity of the sensory stimulation based on the ratio.

Another aspect of the present disclosure relates to a method for enhancing non-rapid eye movement (NREM) sleep by delivering sensory stimulation to a subject during a sleep session with an enhancement system. The system comprises first and second sensors, one or more sensory stimulators, and one or more hardware processors coupled to the first and second sensors and the one or more sensory stimulators. The method comprises: generating, with the first and second sensors, output signals conveying information related to brain activity of the subject during the sleep session, the first and second sensors configured to engage a forehead of the subject. The method comprises detecting, with the one or more hardware processors, NREM sleep in the subject during the sleep session based on the output signals from the first and second sensors. The method comprises controlling, with the one or more processors, the one or more sensory stimulators to provide the sensory stimulation to the subject during the NREM sleep to enhance the NREM sleep in the subject during the sleep session.

In some embodiments, the first sensor comprises a mid-frontal (FPz) electrode, and the second sensor comprises a right ocular electrode (EOGR) or a left ocular electrode (EOGL). In some embodiments, either the first sensor or the second sensor is a reference electrode.

In some embodiments, the method further comprises obtaining, with the one or more hardware processors, historical sleep depth information for a population of users, the historical sleep depth information being related to brain activity of the population of users that indicates sleep depth over time during sleep sessions of the population of users. The method further comprises causing, with the one or more hardware processors, a neural network to be trained based on the historical sleep depth information by providing the historical sleep depth information as input to the neural network. The method further comprises causing, with the one or more hardware processors, based on the output signals from the first and second sensors, the trained neural network to predict future times during the sleep session at which the subject will be in a deep sleep stage, the trained neural network comprising an input layer, an output layer, and one or more intermediate layers between the input layer and the output layer. The method further comprises determining, with the one or more hardware processors, with respect to each of the future times, a predicted sleep stage generated by the output layer of the trained neural network, and sleep stage probability values generated by the one or more intermediate layers of the trained neural network. The method further comprises, responsive to (1) the predicted sleep stage being N3, or (2) the predicted sleep stage being N2 with a ratio of a probability of N3 sleep to a probability of N2 sleep being at least 0.5, causing, with the one or more hardware processors, the one or more sensory stimulators to provide the sensory stimulation to the user at the future times and to modulate a timing and/or intensity of the sensory stimulation during the sleep session based on the one or more probability values generated by the one or more intermediate layers.

In some embodiments, the method further comprises detecting, with the one or more hardware processors, sleep micro-arousals based on the information in the output signals from the first and second sensors, and controlling, with the one or more hardware processors, based on the detected sleep micro-arousals, the one or more sensory stimulators to provide the sensory stimulation to the subject during N3 sleep to enhance the N3 sleep in the subject during the sleep session. A sleep micro-arousal is detected: responsive to a breach of a threshold on a power in a power band of an electroencephalogram (EEG), or based on an additional output from the trained neural network.

In some embodiments, the method further comprises detecting, with the one or more hardware processors, slow waves based on the information in the output signals from the first and second sensors, and controlling, with the one or more hardware processors, based on the detected slow waves, the one or more sensory stimulators to provide the sensory stimulation to the subject during N3 sleep to enhance the N3 sleep in the subject during the sleep session. A slow wave is detected responsive to a breach of a slow wave minimum peak threshold on a negative going electroencephalogram (EEG) signal, responsive to a breach of a slow wave minimum peak threshold on a filtered negative going EEG signal, wherein the filtering boosts a delta portion of the negative going EEG signal, or based on a comparison of a shape of the filtered negative going EEG signal to a shape of a corresponding slow wave template.

In some embodiments, the one or more intermediate layers of the trained neural network are configured to generate additional values from two or more corresponding convolutional layers. In some embodiments, the method further comprises determining, with the one or more hardware processors, a ratio of a value from one convolutional layer to a value from another convolutional layer, and causing, with the one or more hardware processors, the one or more sensory stimulators to modulate the timing and/or intensity of the sensory stimulation based on the ratio.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
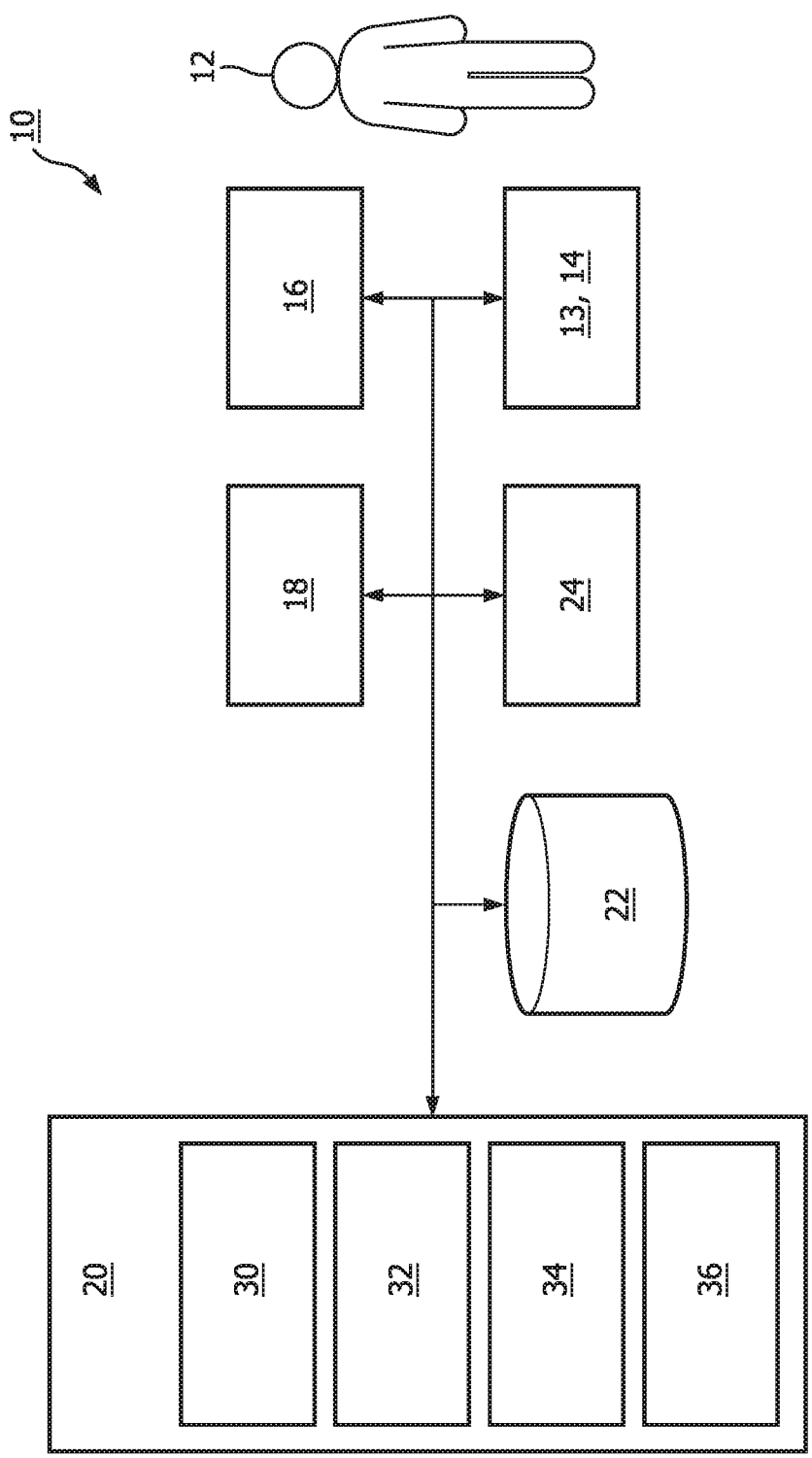
FIG. 1 is a schematic illustration of a system configured to enhance non-rapid eye movement (NREM) sleep and/or other sleep by delivering sensory stimulation to a subject during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a subject 12 during a sleep session. System 10 is configured to enhance deep non-rapid eye movement (NREM) sleep and/or other sleep by delivering sensory stimulation to subject 12 during a sleep session. System 10 is configured to facilitate delivery of sensory stimulation to subject 12 to enhance the restorative effects of sleep in subject 12 and/or for other purposes. System 10 is configured such that sensory stimulation including auditory and/or other stimulation delivered during sleep enhances slow waves in subject 12 without causing arousals, which brings cognitive benefits and enhancement of sleep restoration, for example. As described herein, in some embodiments, system 10 is configured to determine periods of deep sleep during a sleep session (e.g., based on output from a neural network and/or other information). In some embodiments, based on such determinations, system 10 is configured to modulate sensory (e.g., auditory) stimulation delivered to subject 12 to enhance sleep slow waves. In some embodiments, periods of deep sleep may be determined in real-time and/or near real-time during a sleep session of subject 12.

Prior closed-loop, electroencephalogram (EEG) based systems that detect deep sleep in real-time and deliver auditory stimulation use an active electrode (e.g., a frontal FPz sensor) located on the forehead of a user and a reference electrode (e.g., an M2 mastoid sensor) located behind the ear of a user. Positioning one electrode on the forehead of the user and one electrode behind the ear of the user increases discomfort for the user during sleep. However, the electrodes in prior systems are positioned in this way because if the electrodes are located too close to each other (e.g., less than about 10 cm apart) any differential signal the electrodes generate has a relatively small amplitude. Until now, a small differential signal was difficult or impossible to use to detect and/or predict sleep stages in a user during a sleep session.

Figure 2A:
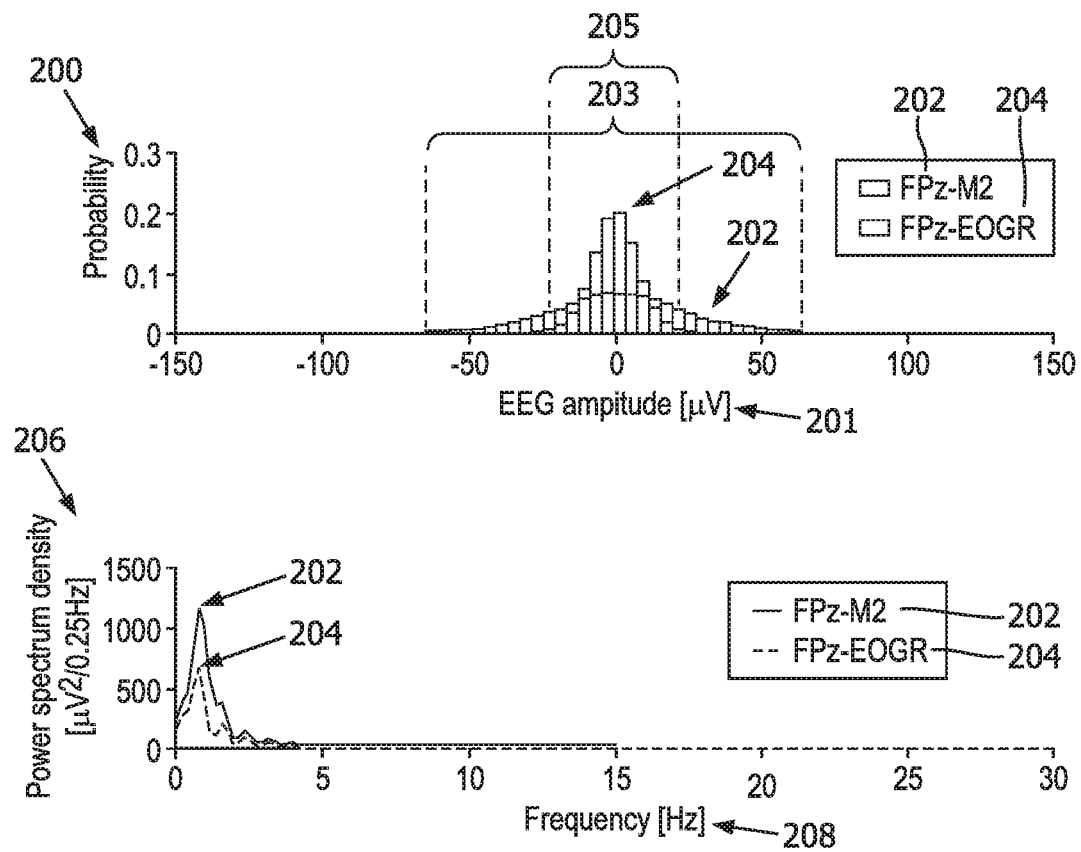
FIG. 2a illustrates an example of the attenuation of a signal amplitude measured between two frontal electrodes (referred to as FP2-EOGR or frontal derivation) compared to the signal amplitude measured between a frontal electrode and a mastoid reference (referred to as FPz-M2), in accordance with one or more embodiments.
Figure 2B:
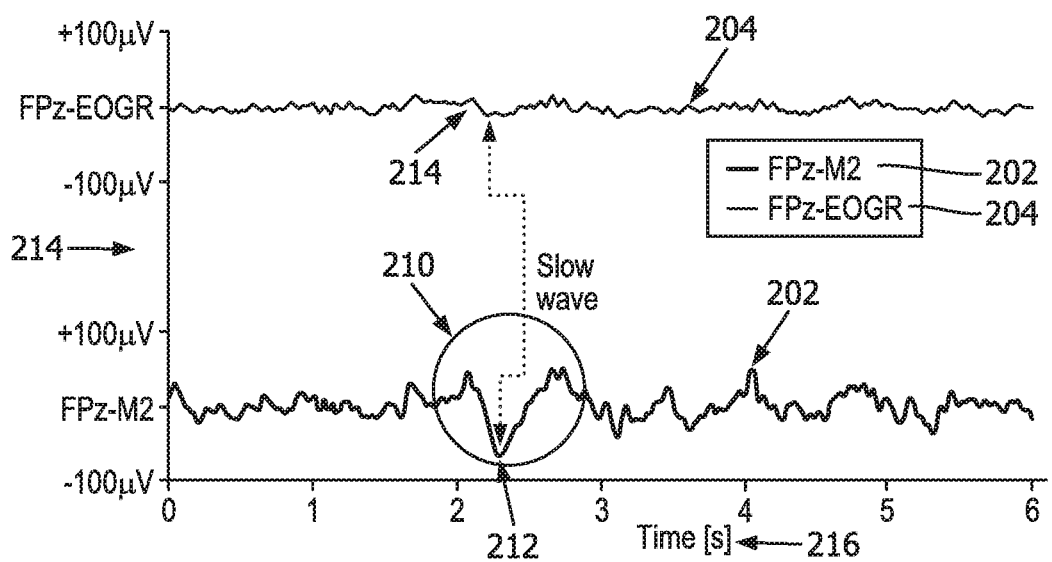
FIG. 2b illustrates an example of the attenuation of a signal indicative of slow waves in the subject measured between the two frontal electrodes (FP2-EOGR) compared to the signal amplitude measured between a frontal electrode and a mastoid reference (FPz-M2), in accordance with one or more embodiments.

For example, as shown in FIGS. 2a and 2b, the attenuation of a signal amplitude measured between two frontal electrodes (e.g., a mid-frontal (FPz) electrode and a right ocular electrode (EOGR), referred to as FPz-EOGR or frontal derivation) compared to the signal amplitude measured between a frontal electrode and a mastoid reference (e.g., referred to as FPz-M2), is noticeable. FIG. 2a (top) illustrates a probability 200 of an EEG amplitude 201 for an FPz-M2 signal 202 and an FPz-EOGR signal 204, and (bottom) a power spectrum density 206 for various frequencies 208 for FPz-M2 signal 202 and an FPz-EOGR signal 204. As shown in FIG. 2a (top), the probability distribution 203 for FPz-M2 signal 202 is wider than the distribution 205 for FPz-EOGR signal 204. Also, (FIG. 2a bottom) the peak power spectrum density 206 for FPz-M2 signal 202 is higher than the peak power spectrum density for FPz-EOGR signal 204. The power spectrum density 206 illustrated in FIG. 2a (bottom) shows that the difference in amplitude primarily manifests in the delta frequency range (0.5 to 4 Hz), which is important for the detection of sleep slow-waves (described below). The attenuation of slow-waves is illustrated in FIG. 2b.

FIG. 2b illustrates an example of the attenuation of a signal indicative of a slow wave 210 in the subject measured between the two frontal electrodes (FP2-EOGR 204) compared to the signal amplitude measured between a frontal electrode and a mastoid reference (FPz-M2 202). FIG. 2b illustrates signals 202 and 204 on a voltage 214 versus time 216 scale. As shown in FIG. 2b, a negative going peak 212 of the FPz-M2 signal 202 (which is indicative of slow wave 210) is more pronounced compared to corresponding features 214 of the FPz-EOGR signal 204.

Figure 3A:
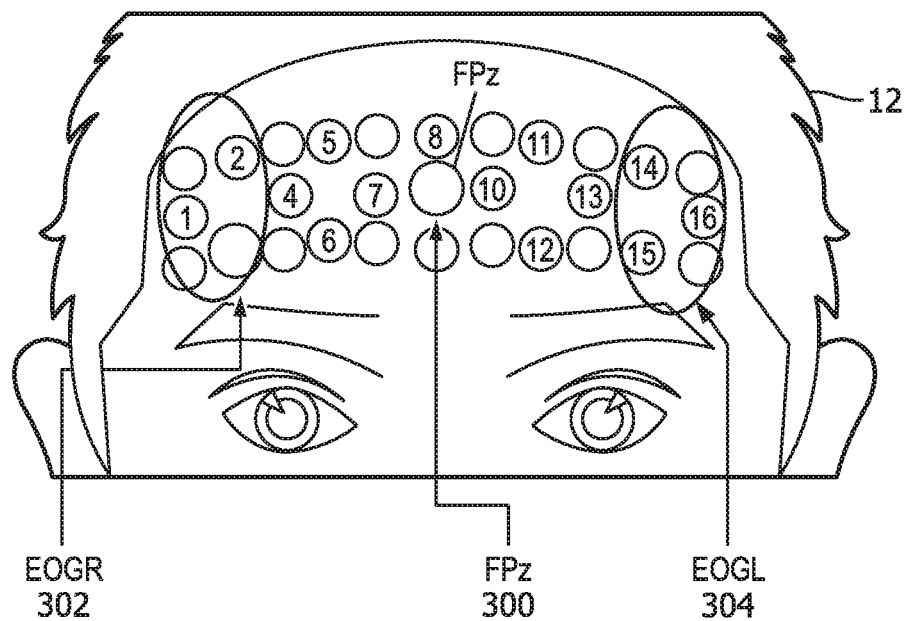
FIG. 3a illustrates an FPz electrode, an EOGR electrode, and an EOGL electrode, all located on the forehead of the subject, in accordance with one or more embodiments.
Figure 3B:
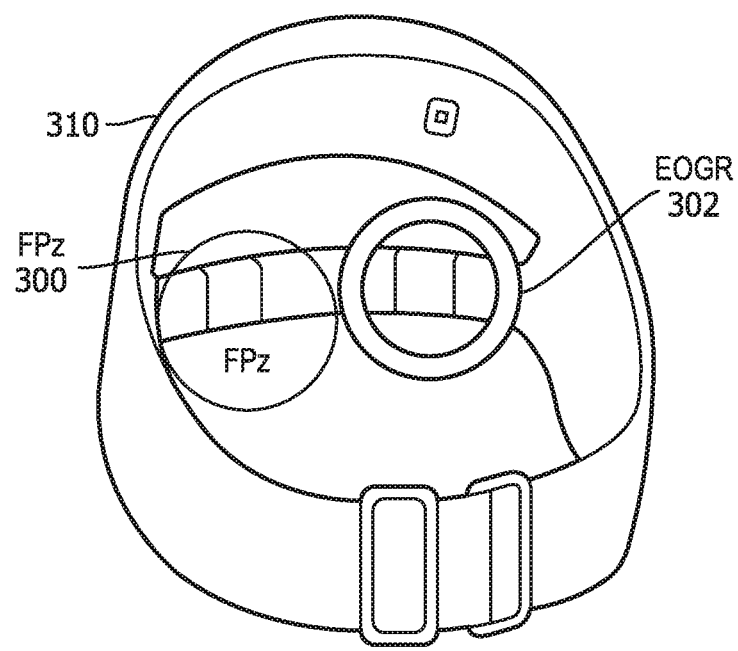
FIG. 3b illustrates a headband that includes the FPz electrode and the EOGR electrode, in accordance with one or more embodiments.

System 10 (FIG. 1) addresses the limitations of prior art systems by replacing the reference electrode traditionally located behind the ear of a user with an electrode located on the forehead of subject 12. For example, FIG. 3a illustrates a mid-frontal (FPz) electrode 300 and a right ocular electrode (EOGR) electrode 302 both located on the forehead of subject 12. FIG. 3a also illustrates a left ocular electrode (EOGL) 304 that may be included in system 10 (e.g., instead of and/or in addition to EOGR electrode 302). FIG. 3b illustrates a headband 310 that includes FPz electrode 300 and EOGR electrode 302. Headband 310 is configured such that FPz electrode 300 and EOGR electrode 302 engage the forehead of subject 12 (FIG. 3a) when headband 310 is worn by subject 12.

Returning to FIG. 1, forehead electrodes increase comfort for subject 12 during sleep sessions and/or may provide other advantages. System 10 is configured to account for the amplitude difference (e.g., FP2-EOGR 204 versus FPz-M2 202 shown in FIGS. 2a and 2b) to detect any sleep stage (e.g., including N3 sleep as described below). System 10 uses information in output signals from frontal sensors (electrodes) configured to engage the forehead of subject 12 in two parallel processes. The first process buffers a temporal window of sensor information, which is processed by system 10 to determine a probable sleep stage associated with the temporal window. In the second process, system 10 determines spectral features from the frontal sensor output signals (e.g. power in the alpha, beta, and delta frequency bands).

System 10 is configured to generate intermediate outputs and probability estimates for individual sleep stage determinations. System 10 is configured to enhance the sleep stage determination accuracy by biasing the sleep stage decisions to meet application specific requirements (e.g., improvement of NREM N3 detection sensitivity at a cost of degrading specificity). System 10 is configured such that if a detected sleep stage (after the staging accuracy enhancement) is N3, then the corresponding frontal signal window is enhanced through a filter that compensates the spectral-dependent amplitude decrease (e.g., shown in FIGS. 2a and 2b). System 10 is configured such that the enhanced signal, in conjunction with intermediate and final outputs from sleep stage determination operations, are used to detect sleep slow-waves and the presence of sleep micro-arousals. The sleep micro-arousals and/or other information are utilized to determine properties of the sensory stimulation. In some embodiments, system 10 includes one or more of sensors 13 and 14, a sensory stimulator 16, external resources 18, a processor 20, electronic storage 22, a user interface 24, and/or other components.

Sensors 13 and 14 are configured to generate output signals conveying information related to brain activity and/or other activity in subject 12. In some embodiments, sensors 13 and 14 are similar to and/or the same as electrodes 300 and/or 302 shown in FIG. 3a, for example. In some embodiments, sensors 13 and 14 are configured to generate output signals conveying information related to brain activity such as slow wave activity in subject 12. In some embodiments, the information related to brain activity and/or other activity in subject 12 is the information related to slow wave activity. In some embodiments, sensors 13 and 14 are configured to generate output signals conveying information related to stimulation provided to subject 12 during sleep sessions. In some embodiments, the information in the output signals from sensors 13 and 14 is used to control sensory stimulator 16 to provide sensory stimulation to subject 12 (as described below).

Sensors 13 and 14 may comprise one or more sensors that generate output signals that convey information related to brain activity in subject 12 directly. For example, sensors 13 and 14 may include electrooculogram (EOG) and/or electroencephalogram (EEG) electrodes (e.g., as described above) configured to detect ocular activity and/or electrical activity along the forehead of subject 12 resulting from current flows within the brain of subject 12. In some embodiments, sensors 13 and 14 are configured to engage the forehead of subject 12 at a distance of less than or equal to 10 centimeters from each other. In some embodiments, one of sensors 13 or 14 comprises a mid-frontal (FPz) electrode, and the other one of sensors 13 or 14 comprises a right ocular electrode (EOGR) or a left ocular electrode (EOGL). In some embodiments, either sensor 13 or sensor 14 is a reference electrode. Although sensors 13 and 14 are illustrated in FIG. 1 at a single location near subject 12, this is not intended to be limiting. Sensors 13 and 14 may include sensors disposed in a plurality of locations, such as for example, within (or in communication with) sensory stimulator 16, coupled (in a removable manner) with clothing of subject 12, worn by subject 12 (e.g., as a headband), and/or in other locations.

In FIG. 1, sensors 13 and 14, sensory stimulator 16, processor 20, electronic storage 22, and user interface 24 are shown as separate entities. This is not intended to be limiting. Some and/or all of the components of system 10 and/or other components may be grouped into one or more singular devices. For example, these and/or other components may be included in a headset and/or other garments worn by subject 12. Such a headset may include, for example, sensing electrodes, a reference electrode, one or more devices associated with an EOG and/or an EEG, means to deliver auditory stimulation (e.g., a wired and/or wireless audio device and/or other devices), and one or more audio speakers. In this example, the audio speakers may be located in and/or near the ears of subject 12 and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to subject 12 via the wireless audio device and/or speakers. In this example, the (EOG and/or EEG) sensing electrodes, the reference electrode, and the EEG devices may be represented, for example, by sensors 13 and 14 in FIG. 1. The wireless audio device and the speakers may be represented, for example, by sensory stimulator 16 shown in FIG. 1. In this example, a computing device may include processor 20, electronic storage 22, user interface 24, and/or other components of system 10 shown in FIG. 1.

Stimulator 16 is configured to provide sensory stimulation to subject 12.

Sensory stimulator 16 is configured to provide auditory, visual, somatosensory, electric, magnetic, and/or sensory stimulation to subject 12 prior to a sleep session, during a sleep session, and/or at other times. In some embodiments, a sleep session may comprise any period of time when subject 12 is sleeping and/or attempting to sleep. Sleep sessions may include nights of sleep, naps, and/or other sleeps sessions. For example, sensory stimulator 16 may be configured to provide stimuli to subject 12 during a sleep session to facilitate a transition to a deeper stage of sleep, a lighter stage of sleep, maintain sleep in a specific stage, enhance the restorative effects of sleep, and/or for other purposes. In some embodiments, sensory stimulator 16 may be configured such that facilitating a transition between deeper sleep stages and lighter sleep stages includes decreasing sleep slow waves in subject 12, and facilitating a transition between lighter sleep stages and deeper sleep stages includes increasing sleep slow waves.

Sensory stimulator 16 is configured to facilitate transitions between sleep stages, maintain sleep in a specific stage, and/or enhance the restorative effects of sleep through non-invasive brain stimulation and/or other methods. Sensory stimulator 16 may be configured to facilitate transitions between sleep stages, maintain sleep in a specific stage, and/or enhance the restorative effects of sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to subject 12 to enhance the restorative effects of sleep in subject 12. The acoustic tones may include one or more series of tones of a determined length separated from each other by an inter-tone interval. The volume (e.g., the intensity) of individual tones may be modulated based on sleep depth and other factors (as described herein) such that loud tones are played during deeper sleep and soft tones are played during lighter sleep. The length of individual tones (e.g., the timing) and/or the inter tone interval (e.g., the timing) may also be adjusted depending on whether subject 12 is in deeper or lighter sleep. This example is not intended to be limiting. Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. For example, external resources 18 may include sources of historical sleep depth information for a population of users, and/or other information. The historical sleep depth information for the population of users may be related to brain activity of the population of users that indicates sleep depth over time during sleep sessions of the population of users. In some embodiments, the historical sleep depth information for the population of users may be related to a user population in a given geographical area; demographic information related to gender, ethnicity, age, a general health level, and/or other demographic information; physiological information (e.g., weight, blood pressure, pulse, etc.) about the population of users, and/or other information. In some embodiments, this information may indicate whether an individual user in the population of user is demographically, physiologically, and/or otherwise similar to subject 12.

In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 18 may be provided by resources included in system 10. External resources 18 may be configured to communicate with processor 20, user interface 24, sensors 13 and 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to partition (or window) the output signals from sensors 13 and 14 and provide the information in the output signals to model component 32 and/or a deep neural network in temporal windows (e.g., as described below). In some embodiments, the temporal windows are about six seconds long, for example. This example is not intended to be limiting. Other temporal windows of time are contemplated. Information component 30 is also configured to determine one or more brain activity parameters of subject 12. The brain activity parameters may be determined by filtering and/or by performing other operations on the information in the output signals from sensors 13 and 14 as described herein. The brain activity parameters indicate depth of sleep in subject 12. In some embodiments, the information in the output signals related to brain activity indicates sleep depth over time. In some embodiments, the information indicating sleep depth over time is or includes information related to power in various bands of an EEG, slow wave activity in subject 12, and/or other information. In some embodiments, information component 30 is configured to determine an EEG for subject 12 based on the information in the output signals from sensors 13 and 14, and/or other information.

In some embodiments, the slow wave activity of subject 12 may be indicative of sleep stages of subject 12. The sleep stages of subject 12 may be associated with rapid eye movement (REM) sleep, non-rapid eye movement (NREM) sleep, and/or other sleep. The sleep stages of the population of users may be one or more of NREM stage N1, stage N2, or stage N3, REM sleep, and/or other sleep stages. In some embodiments, the sleep stages of subject 12 may be one or more of stage S1, S2, S3, or S4. In some embodiments, NREM stage 2 and/or 3 (and/or S3 and/or S4) may be slow wave (e.g., deep) sleep. In some embodiments, the information related to brain activity that indicates sleep depth over time is and/or is related to one or more additional brain activity parameters.

In some embodiments, the information related to brain activity that indicates sleep depth over time is and/or includes EEG and/or other information generated during sleep sessions of a population of users. In some embodiments, brain activity parameters may be determined based on the EEG information. In some embodiments, the brain activity parameters may be determined by information component 30 and/or other components of system 10. In some embodiments, the brain activity parameters may be previously determined and be part of historical sleep depth information obtained from external resources 18. In some embodiments, the one or more brain activity parameters are and/or are related to a frequency, amplitude, phase, presence of specific sleep patterns such as spindles, K-complexes, or sleep slow waves, alpha waves, power in various bands, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above. For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present. In some embodiments, slow wave activity is a continuous value (e.g., EEG power in the 0.4 to 4 Hz band), which is positive. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and SWA are the same when considering sleep EEG. In some embodiments, the information related to brain activity that indicates sleep depth over time indicates changes in an EEG delta power over time, a quantity of micro arousals in the population of users, other EEG power levels, and/or other parameters.

Information component 30 is configured to obtain the historical sleep depth information. In some embodiments, the historical sleep depth information is for the population of users. In some embodiments, the historical sleep depth information is for subject 12. The historical sleep depth information is related to brain activity of the population of users and/or subject 12 that indicates sleep depth over time during previous sleep sessions of the population of users and/or subject 12. The historical sleep depth information is related to sleep stages and/or other brain activity parameters of the population of users and/or subject 12 during corresponding sleep sessions, and/or other information. In some embodiments, information component 30 is configured to obtain the historical sleep depth information electronically from external resources 18, electronic storage 22, and/or other sources of information. In some embodiments, obtaining the historical sleep depth information electronically from external resources 18, electronic storage 22, and/or other sources of information comprises querying one more databases and/or servers; uploading information and/or downloading information, facilitating user input (e.g., criteria used to define a target patient population input via user interface 24), sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep depth information (e.g., length of sleep sessions, number of sleep sessions, etc.) and/or perform other operations.

Model component 32 is configured to cause a machine-learning model to be trained using the historical sleep depth information. In some embodiments, the machine-learning model is trained based on the historical sleep depth information by providing the historical sleep depth information as input to the machine-learning model. In some embodiments, the machine-learning model may be and/or include mathematical equations, algorithms, plots, charts, networks (e.g., neural networks), and/or other tools and machine-learning model components. For example, the machine-learning model may be and/or include one or more neural networks having an input layer, an output layer, and one or more intermediate or hidden layers. In some embodiments, the one or more neural networks may be and/or include deep neural networks (e.g., neural networks that have one or more intermediate or hidden layers between the input and output layers).

As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

As described above, the trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. In some embodiments, the trained neural network may comprise a deep neural network comprising a stack of convolution neural networks, followed by a stack of long short term memory (LSTM) elements, for example. The convolutional neural network layers may be thought of as filters, and the LSTM layers may be thought of as memory elements that keep track of sleep stage history, for example. The deep neural network may be configured such that there are max pooling layers which reduce dimensionality between the convolutional neural network layers. In some embodiments, the deep neural network comprises optional scalar parameters (like body-mass-index BMI, gender, age, etc.) before the LSTM layers. In some embodiments, the deep neural network comprises dense layers, on top of the convolutional layers and recurrent layers. In some embodiments, the deep neural network may comprise additional hyper-parameters, such as dropouts or weight-regularization parameters, for example.

The predicted sleep stages and/or future times of deep sleep stages are generated based on the information in the output signals from sensors 13 and 14 as processed by the layers of the neural network. In some embodiments, outputs of the deep neural network include (soft) probability values for individual sleep stages for individual windows. Model component 32 is configured such that these probability values may be transformed via the ARGMAX operator (for example) into a hard decision sleep stage value for each window.

Model component 32 is configured such that the trained (e.g., deep) neural network and/or any other supervised machine learning algorithms are caused to detect, and/or indicate predicted, sleep stages for subject 12. In some embodiments, this may be and/or include (1) determining periods when subject 12 is experiencing NREM stage N3 or N2 sleep during the sleep session; predicting future times during the sleep session at which subject 12 will be in a deep (NREM) sleep stage, and/or other operations. The determined and/or predicted sleep stages and/or timing indicates whether the user is in (or will be in) deep sleep for stimulation and/or other information. By way of a non-limiting example, a trained neural network may be caused to indicate predicted sleep stages and/or future times and/or timing of the deep sleep stages for subject 12 based on the output signals (e.g., using the information in the output signals as input for the model) and/or other information. The trained neural network is configured to indicate sleep stages occurring, or predicted to occur at future times, for subject 12 during the sleep session. In some embodiments, as described above, information component 30 in conjunction with model component 32 is configured to provide the information in the output signals to the neural network in temporal sets (windows) that correspond to individual periods of time during the sleep session. Model component 32 is configured to cause the trained neural network to output the determined and/or predicted sleep stages, and/or predicted times of deep sleep stages for subject 12, during the sleep session based on the temporal sets of information. Model component 32 is further described below with respect to FIG. 4-FIG. 8.

Control component 34 is configured to control stimulator 16 to provide stimulation to subject 12 during sleep and/or at other times. Control component 34 is configured to cause sensory stimulator 16 to provide sensory stimulation to subject 12 based on a detected and/or predicted sleep stage, future times at which subject 12 will be in a deep sleep stage, and/or other information over time during the sleep session. Control component 34 is configured to cause sensory stimulator 16 to provide sensory stimulation to subject 12 responsive to subject 12 being in, or likely being in, deep NREM sleep for stimulation (e.g., deep N3 sleep). Control component 34 is configured to control one or more sensory stimulators 16 to provide the sensory stimulation to subject 12 during deep NREM sleep to enhance the deep NREM sleep in subject 12 during the sleep session.

For example, control component 34 is configured such that controlling one or more sensory stimulators 16 to provide the sensory stimulation to subject 12 during deep NREM sleep to enhance the deep NREM sleep in subject 12 during the sleep session comprises: determining, with respect to (1) the periods when subject 12 is experiencing deep NREM N3 sleep, or (2) each of the future times, based on one or more values generated by the one or more intermediate layers of the trained neural network, whether subject 12 is in, or will likely be in N3 sleep; causing one or more sensory stimulators 16 to provide the sensory stimulation to subject 12 (1) during the periods when subject 12 is experiencing deep (e.g., N3) NREM sleep, or (2) at the future times, and determining, and/or causing one or more sensory stimulators 16 to modulate (e.g., as described herein), an amount, a timing, and/or intensity of the sensory stimulation provided to subject 12 based on the one or more values of the one or more intermediate layers and/or other information. In some embodiments, stimulators 16 are controlled by control component 34 to enhance deep NREM sleep through (e.g. peripheral auditory, magnetic, electrical, and/or other) stimulation delivered during deep NREM sleep (as described herein). On detection of sleep stage transitions (e.g., from deep NREM sleep to some other sleep stage), control component 34 is configured to stop stimulation. Control component 34 is further described below with respect to FIG. 4-FIG. 8.

Modulation component 36 is configured to cause sensory stimulator 16 to modulate a timing and/or intensity of the sensory stimulation. Modulation component 36 is configured to cause sensory stimulator 16 to modulate the timing and/or intensity of the sensory stimulation based on the brain activity parameters, values output from the (output and/or intermediate) layers of the trained neural network, and/or other information. As an example, sensory stimulator 16 is caused to modulate the timing and/or intensity of the sensory stimulation based on the brain activity parameters, the values output from the convolutional layers, the values output from the recurrent layers, and/or other information. In some embodiments, parameters determined (e.g., by information component 30 shown in FIG. 1) based on the raw EEG signal (e.g., also determined by information component 30) can be used to modulate stimulation settings. As described above, these parameters include sleep depth parameters (e.g., a ratio between the EEG power in the delta band and the EEG power in the beta band), the density of detected slow-waves per unit of time, the power in the delta band, and/or other parameters. Modulation component 36 is further described below with respect to FIG. 4-FIG. 8.

Figure 4:
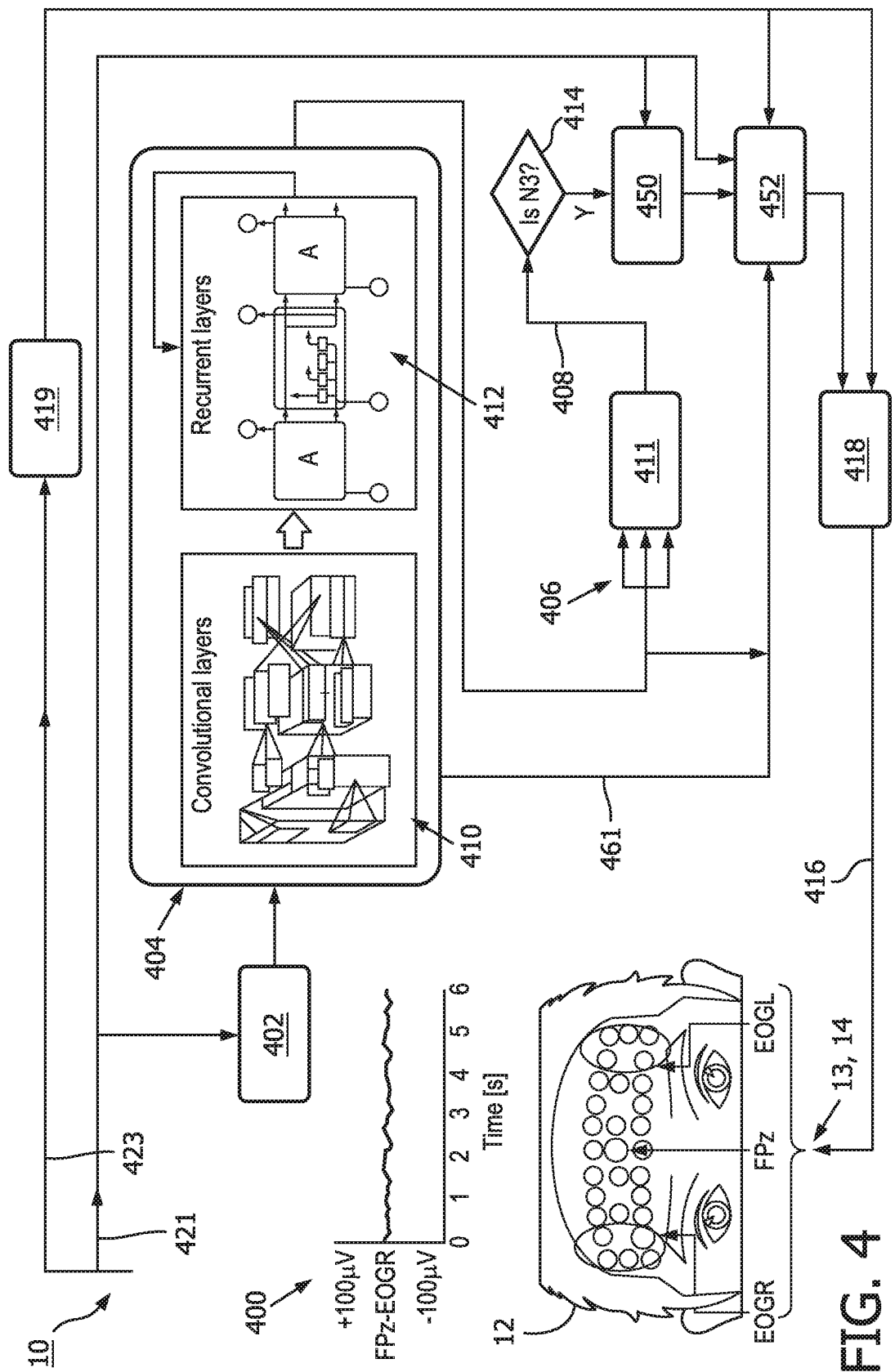
FIG. 4 illustrates several of the operations performed by the system, in accordance with one or more embodiments.

By way of a non-limiting example, FIG. 4 illustrates several of the operations performed by system 10 and described above. In the example shown in FIG. 4, a frontal signal 400 (from sensors 13 and 14 engaged with the forehead of subject 12) is processed and/or otherwise provided (e.g., by information component 30 and model component 32 shown in FIG. 1) to a deep neural network 404 in temporal windows 402. Deep neural network 404 predicts 406 future sleep stages and/or future times where subject 12 will be in deep sleep based on the information in temporal windows 402. The architecture of deep neural network 404 includes convolutional layers 410 (which can be thought of as filters) and recurrent layers 412 (which, as just one example, may be implemented as long-short term memory elements) that endow network 404 with memory to be able to use past predictions to refine prediction accuracy. A sleep stage prediction accuracy enhancement operation 411 (performed by control component 34 shown in FIG. 1 as part of causing sensory stimulator 16 to provide sensory stimulation to subject 12 based on a detected and/or predicted sleep stage—further described below) follows sleep stage prediction 406. Predicting future sleep stages and/or timing of deep sleep stages, and enhancing the accuracy of these predictions, facilitates provision of sensory stimulation to enhance slow wave sleep because it enables system 10 to either withhold stimulation (if lighter sleep stages are predicted) or prepare for stimulation with optimized timing and intensity when deeper (e.g., NREM) sleep is predicted.

As shown in FIG. 4, system 10 uses information in frontal signal 400 in two parallel processes. As described above, a first process 421 includes buffering a temporal window 402 of sensor information 402, which is processed by deep neural network 404 to determine a probable sleep stage associated with temporal window 402. A second process 423, includes determining 419 (e.g., by information component 30 shown in FIG. 1) spectral features (e.g., parameters as described above) from frontal signal 400 (e.g. power in the alpha, beta, and delta frequency bands).

Responsive to enhanced sleep stage predictions 408 indicating NREM stage N3 sleep is predicted (e.g., deep sleep for the provision of sensory stimulation) 414, windowed frontal signal 400 is enhanced 450; slow waves, micro-arousals, and/or other characteristics of the enhanced windowed frontal signal are detected 452; and stimulation 416 is provided to subject 12 (e.g., from sensory stimulator 16 controlled by control component 34 shown in FIG. 1). The slow waves and micro-arousals are detected in part based on the determined spectral features 419 from second process 423, intermediate outputs 461 from deep neural network 404, sleep stages predicted 406 by deep neural network 404, and/or other information. The intensity and/or timing of stimulation 416 is modulated 418 (e.g., by modulation component 36) based on parameters 419 (e.g., determined by information component 30 shown in FIG. 1), detected slow waves and/or micro-arousals 452, enhanced predicted N3 sleep 450, and/or other information. As described above, in some embodiments, the sensory stimulation comprises audible tones. In these embodiments, sensory stimulators 16 may modulate the timing and/or intensity of the sensory stimulation by decreasing an inter tone interval and/or increasing a tone volume.

Referring to FIG. 1 and FIG. 4, a useful property of neural networks is that they can produce probabilities associated with pre-defined sleep stages (e.g. Wake, REM, N1, N2, N3 sleep). Model component 32 is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems). Model component 32 is configured such that both the values output from convolutional layers, and the soft decision value outputs, are vectors comprising continuous values as opposed to discrete values such as sleep stages. Consequently, convolutional and recurrent (soft-decision) value outputs are available to be used by system 10 to determine and/or predict sleep stages, modulate the volume of the stimulation, and/or perform other operations, for example.

Model component 32 is configured to determine, with respect to individual future times during a sleep session, a predicted sleep stage generated by the output layer of the trained neural network, and sleep stage probability values generated by the one or more intermediate layers of the trained neural network (e.g., 406 in FIG. 4). As described above, system 10 is configured to enhance (e.g., 411 shown in FIG. 4) N3 detection accuracy so that sensors 13 and 14 may both be placed on the forehead of subject 12 during a sleep session. Improving N3 detection sensitivity is accomplished by considering the probability ratio between N2 and N3 sleep for each individual future time.

For example, in system 10, control component 34 is configured, responsive to (1) the predicted sleep stage being N3 (e.g., output from the output layer of the trained neural network), or (2) the predicted sleep stage being N2 with a ratio of a probability of N3 sleep to a probability of N2 sleep being at least 0.5 (this example is not intended to be limiting), to cause sensory stimulator 16 to provide the sensory stimulation to subject 12 at the future times (and/or to modulate a timing and/or intensity of the sensory stimulation during the sleep session based on the one or more probability values generated by the one or more intermediate layers as described herein). Control component 34 may be thought of as performing a post-processing step (e.g., 411 from FIG. 4) on soft outputs (probabilities) of the trained (deep) neural network. For a window where the N2 probability is the highest and N3 probability is the second highest, when the ratio between the probability of N3 and the probability of N2 is greater than 0.5 (for example), control component 34 is configured to assign N3 sleep to that window (instead of N2, even though N2 had the highest probability and would have been the sleep stage predicted by the trained neural network by itself).

In some embodiments, control component 34 is configured to detect sleep micro-arousals (e.g., at operation 450 in FIG. 4) based on the information in the output signals from sensors 13 and 14 and/or other information, and control, based on the detected sleep micro-arousals, one or more sensory stimulators 16 to provide the sensory stimulation to subject 12 during N3 sleep to enhance the N3 sleep in subject 12 during the sleep session (e.g., 416 in FIG. 4). Controlling one or more sensory stimulators 16 based on detected micro-arousals may include modulating an intensity of the sensory stimulation provided to subject 12 and/or other control (e.g., 418 in FIG. 4). Control component 34 may be configured such that, if a micro-arousal is detected during stimulation, the delivery of sensory stimulation is paused for a predefined period of time (e.g., 10 secs). In some embodiments, a sleep micro-arousal is detected responsive to a breach of a threshold on a power in a power band of the EEG, based on an additional output from the trained neural network, and/or based on other information.

By way of a non-limiting example, control component 34 may be configured such that (preprocessed) EEG signals (e.g., output signals from sensors 15, 16) are band-pass filtered in the $\alpha$-band (in this particular example the filter uses the 8-14.5 Hz band) and $\beta$-band (e.g., 19-24 Hz). Control component 34 may use these signals to generate $\alpha$-band and $\beta$-band RMS (root mean square) values that are estimated every 1.5 seconds (for example, and/or any other amount of time that allows system 10 to function as described herein). A candidate (or possible) micro-arousal is flagged by control component 34 when any single $\alpha$ or $\beta$ RMS sample is above a respective threshold. If a candidate micro-arousal persists for longer than an arousal refractory period (e.g., two consecutive seconds and/or any other length of time that allows system 10 to function as described herein), then the event is flagged as a detected micro-arousal.

Figure 5:
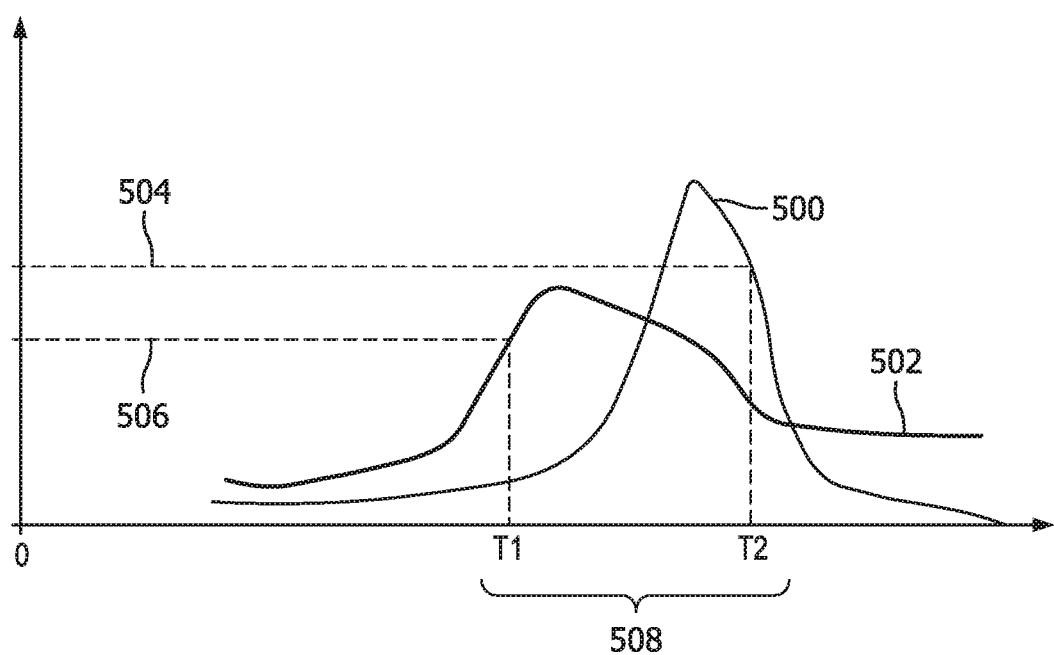
FIG. 5 illustrates micro-arousal detection, in accordance with one or more embodiments.

An example of micro-arousal detection is shown in FIG. 5. FIG. 5 illustrates $\alpha$-band 500 and $\beta$-band 502 RMS values, corresponding thresholds 504 (e.g., 7) and 506 (e.g., 0.9), and an arousal refractory period 508 (T2–T1). As described above, a candidate (or possible) micro-arousal is flagged by control component 34 (FIG. 1) when any single $\alpha$ or $\beta$ RMS value 500, 502 is above a corresponding threshold 504, 506. If a candidate micro-arousal persists for longer than arousal refractory period 508, then the event is flagged as a detected micro-arousal. In some embodiments, control component 34 may be configured such that detected micro-arousals in close time proximity to each other (e.g., within a three second interval between the end of a first detected micro-arousal and the beginning of a second micro-arousal) are merged.

Returning to FIGS. 1 and 4, in some embodiments, control component 34 is configured such that the thresholds for $\alpha$ and $\beta$ are determined using a parameter optimization procedure configured to match micro-arousals manually annotated by a trained sleep technician. Raw output signals (e.g., from sensors 13, 14) are run through software designed to simulate sleep stage determination (e.g., the trained neural network described above). Several different combinations of alpha $\in\{5:12;$ step=1$\}$ and beta E $\{0.6:2,$ step=0.1$\}$ thresholds can be tested by the simulator. The arousals detected in the periods of N3 sleep (automatically detected as described above) are compared against arousals manually annotated by a sleep technician in the same period. As non-limiting examples, sensitivity, specificity, positive predictive value (PPV), and area under the receiver operating characteristic (ROC) curve (area under the curve—AUC) may be determined to quantify micro-arousal detection performance and facilitate selection of an optimal alpha-beta combination. In some embodiments, an optimal alpha threshold may be 7 ($\alpha$=7), and an optimal beta threshold may be 0.9 ($\beta$=0.9), but these examples are not intended to be limiting.

In some embodiments, control component 34 is configured to use one or more deep neural networks to detect sleep micro-arousals. A deep neural network used to detect sleep micro-arousals may be similar to and/or the same as the deep neural network described above. Similarly, the deep neural network may include one or more convolution neural networks (CNN) and long short term memory (LSTM), with optional dense layers, and/or other architecture. This architecture may require segmenting output signals into time windows (e.g., windowing in three second windows—this example is not intended to be limiting). For clarification, in system 10, three types of windows are considered: a (e.g., six second) window to detect sleep stages; a (e.g., 1.5 second) window to detect micro-arousals based on the power in the beta/alpha band; and a (e.g., 3-second long) window to detect micro-arousals based on the deep-learning based detector. In some embodiments, control component 34 is configured to address micro-arousal arousal detection as a binary classification problem. The arousal detection problem is highly imbalanced, meaning that arousal and non-arousal samples are not always of equal size. In some embodiments, an arousal-detection DNN uses as input, a (e.g., 3-second) window comprising EEG samples (not band powers). For each of these windows, the DNN produces a yes/no output (i.e. binary decision) defining whether an arousal was detected or not. The DNN is trained with sleep data that was previously annotated by an expert sleep technician for the presence of arousals. The imbalance issue (more non-arousals compared to arousals) is due to the fact that in a typical sleep night from a healthy user, more 3-second windows without arousal are found compared to 3-second windows containing arousals.

In some embodiments, control component 34 is configured to detect slow waves based on the information in the output signals from sensors 13 and 14 (e.g., at operation 450 in FIG. 4), and control, based on the detected slow waves, one or more sensory stimulators 16 to provide the sensory stimulation to the subject during N3 sleep to enhance the N3 sleep in the subject during the sleep session (e.g., 416 shown in FIG. 4). In some embodiments, a slow wave is detected responsive to a breach of a slow wave minimum peak threshold on a negative going EEG signal, responsive to a breach of a slow wave minimum peak threshold on a filtered negative going EEG signal (where the filtering boosts a delta portion of the negative going EEG signal), and/or based on a comparison of a shape of the filtered negative going EEG signal to a shape of a corresponding slow wave template.

Figure 6:
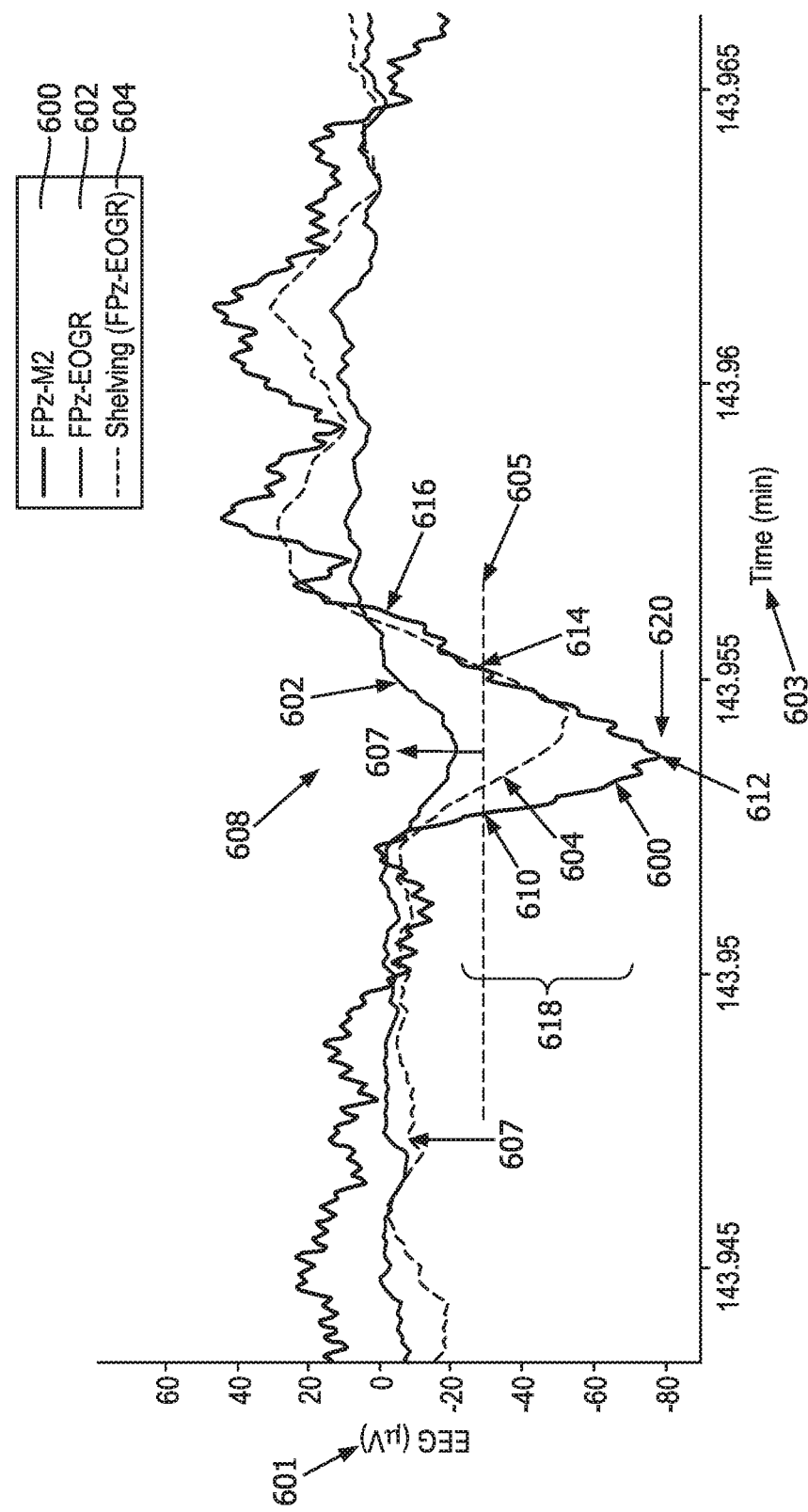
FIG. 6 illustrates different EEG signals showing slow waves, in accordance with one or more embodiments.

By way of a non-limiting example, FIG. 6 illustrates different EEG 601 signals 600, 602, 604 over time 603 showing slow waves 608, in accordance with one or more embodiments. In prior systems that generate the typical FPz-M2 electrode signal 600, real-time detection of sleep slow waves is accomplished by sampling four points 610, 612, 614, 616 from a negative going portion 618 of an EEG signal (e.g., 602) with a minimum peak 620 breaching a configurable threshold value 605. As shown in FIG. 6, the sampled points of interest 610, 612, 614, and 616 are collected at indices where the negative threshold 605 is first breached, at the negative peak 620, at the point of returning to the negative threshold (with positive slope) 605, and at the point of a subsequent positive-going zero-crossing. The sampled points are subsequently used to estimate the frequency of a corresponding sinusoid that passes through the points, as well as through the positive zero-crossing, yielding three frequency estimations corresponding to the candidate sleep slow wave. The average frequency estimation is then compared against bounding thresholds in order to qualify or disqualify the windowed signal as a slow-wave. As an example, a typical prior system may use a minimum threshold (e.g., 605) of 29 μV during slow wave detection.

In system 10 (FIG. 1), which includes sensors 13 and 14 (FIG. 1) configured to engage the forehead of subject 12 (e.g., a frontal derivation system), a power spectral density analysis shows that the delta band (0.5 to 4 Hz) amplitudes are more prominently reduced compared to adjacent frequency bands. This is illustrated in FIG. 6 by FPz-EOGR signal 602. Slow wave 608 appears much shallower in signal 602 relative to signal 600. Thus, in order to detect slow waves, system 10 is configured to operate with different thresholds, and/or configured to detect slow waves in different ways. For example, system 10 is configured to detect slow-waves, even with the reduced amplitudes found in the frontal derivation signal, using one or more of the following possible approaches.

In some embodiments (e.g., a first example approach), control component 34 (FIG. 1) is configured to reduce 607 the slow-wave minimum peak threshold 605 until slow wave sensitivity is regained. The decrease in the threshold for the slow-wave peak, increases sensitivity as more slow-wave events can be detected. Control component 34 may be configured to sample points of interest (e.g., similar to 610, 612, 614, and 616, but for signal 602) for a frontal signal (e.g., signal 602, the output signals of sensors 13 and 14 shown in FIG. 1) at indices where a negative threshold (e.g., selected for signal 602) is first breached, at a negative going peak in the signal, at the point of returning to the negative threshold (with positive slope) in the signal, and at the point of a subsequent positive-going zero-crossing in the signal. The sampled points in the frontal signal (e.g., 602) are subsequently used to estimate the frequency of a corresponding sinusoid that passes through the points, as well as through the positive zero-crossing, yielding three frequency estimations corresponding to the candidate sleep slow wave. The average frequency estimation is then compared against bounding thresholds for the frontal signal in order to qualify or disqualify the windowed signal as a slow-wave.

In some embodiments, (e.g., a second example approach), control component 34 is configured to cause and/or retain disparity between the amplitudes of delta and non-delta frequency components typically found in N3 deep sleep. Given that the frontal derivation signal (e.g., 602 shown in FIG. 6) has an asymmetric reduction in amplitudes across the frequency spectrum, control component 34 is configured to boost the delta and nearby frequencies via a shelving filter (e.g., operation 450 shown in FIG. 4). This boosted signal is illustrated by signal 604 in FIG. 6. As shown in FIG. 6, signal 604 is shallower (e.g., has a less negative minimum) at slow waves 608 compared to signal 600, but deeper (e.g., a more negative minimum) compared to signal 602. Control component 34 (FIG. 1) is configured to determine the slow-wave minimum peak threshold for boosted signal 604 to facilitate detection of slow waves. This threshold, for example, may be between corresponding thresholds for signals 600 and 602. The slow-wave minimum peak threshold for boosted signal 604 may be used as the thresholds (e.g., 605) described in the paragraphs above to facilitate detection of slow waves.

In some embodiments, (e.g., a third example approach) control component 34 (FIG. 1) is configured such that the delta-boosting described above is combined with a different slow-wave detection algorithm. As shown in FIG. 6, an EEG determined from frontal signal 602 often has a different morphology than a reference signal (FPz-M2) 600. In some embodiments, the frontal signal is substantially smaller compared to the signal with reference to the mastoid. The frontal signal is not just simply scaled down but its spectral properties are also different (e.g., it has a different morphology—see FIG. 2). In some embodiments, control component 34 is configured such that windows of EEG containing candidate slow waves are sampled and normalized for comparison to a template slow wave. The template slow wave may be determined based on information from previous sleep sessions of subject 12; determined based on information from previous sleep sessions of other (e.g., demographically similar) users; determined based on entries and/or selections (e.g., via user interface 24) made by a caregiver, subject 12, and/or other users; and/or determined in other ways (e.g., as described below). Control component 34 is configured such that the template comprises an identical number of sampled points (to the number of sampled points sampled from the EEG windows), and is determined by collecting (e.g., FPz-EOGR) signals at locations where a reference (e.g., FPz-M2) signal includes a slow-wave, and averaging the collected signals. Once a candidate slow wave is detected (e.g., as described above, with further information provided below), the mean and/or standard deviation of the point-by-point error (as normalized and compared to the template) are used to determine whether the candidate is morphologically similar enough to the template to be considered a slow wave. In some embodiments, candidate slow waves are pre-screened by control component 34 via thresholds for their duration, and a minimum negative threshold similar to the methods described above. Examples of template selection, template normalization, identification of potential slow waves, normalization of potential slow waves, and comparison with a template are described below.

Template Selection: control component 34 (FIG. 1) is configured such that a slow-wave template need only be determined once (but multiple template determinations and redeterminations are contemplated), and may be re-used across subjects and sleep session datasets. The slow-wave template used for automated detection may be determined by selecting the template from real subject datasets, determining the template based on a mean of slow waves which have been automatically detected using other methods, manually constructed from desired waveform features, and/or determined in other ways.

Template Normalization: control component 34 is configured such that, after a template has been determined, the template is decimated by selecting k evenly spaced points from the template. The choice of k is determined based on a trade-off between real-time processing needs, and template resolution. The value of k may be about 16, for example. The voltage range for the template slow wave is normalized from a peak voltage [0s, vPeak] to a target voltage [0, e.g., −40 μV]. The value of k, the target voltage, and/or other parameters may be determined based on information from prior sleep sessions of subject 12 and/or other users, entered and/or selected by a caregiver, subject 12, and/or other users, and/or determined in other ways.

Identification of Potential Slow-Waves: control component 34 (FIG. 1) is configured such that a potential slow-wave is determined to be any waveform segment that has the following characteristics, and lies below 0 μV: a positive-to-negative zero crossing, a subsequent negative peak below −40 μV, and a subsequent return (in voltage) to a predetermined percentage of the negative peak amplitude. For example, the predetermined percentage may be 0%, indicating that a potential slow wave would be identified when the voltage of the waveform reaches the negative to positive zero crossing (e.g., similar to point 616 in FIG. 6), 100%, indicating that a potential slow wave would be identified when the voltage of the waveform is at the negative peak (e.g., similar to point 612 in FIG. 6), 50%, indicating that a potential slow wave would be identified when the voltage of the waveform is half way between the negative peak and the subsequent zero crossing (e.g., similar to point 614 in FIG. 6), and/or other percentages. The predetermined percentage may be determined based on information from prior sleep sessions of subject 12 and/or other users, entered and/or selected by a caregiver, subject 12, and/or other users, and/or determined in other ways.

Normalization of Potential Slow-Waves: control component 34 (FIG. 1) is configured such that, once a potential slow-wave is identified, the candidate waveform is normalized in an identical manner to the template normalization above. Control component 34 is configured such that the waveform is decimated by selecting k evenly spaced points from the template (where the choice of k is determined based on the trade-off between real-time processing needs and template resolution, and the value of k may be about 16, for example), and the range is normalized from [0, vPeak] to the target range (e.g., [0, −40 μV]).

Comparison with the Template: control component 34 (FIG. 1) is configured to compare a potential slow wave to the template using the mean and/or standard deviation of the point-by-point error, and/or using other methods. For example, in some embodiments, control component 34 is configured to use the mean of point by point differences between the potential slow wave and the template by determining the point by point voltage differences between a candidate waveform and the template ($V_{diff}=V_{candidate}-V_{template}$), determining the mean of these differences in units of microvolts, for example ($\mu$=mean ($V_{diff}$)), and validating the candidate waveform based on whether the mean breaches a threshold on the mean. The threshold on the mean may be determined based on information from prior sleep sessions of subject 12 and/or other users, entered and/or selected by a caregiver, subject 12, and/or other users, and/or determined in other ways.

As another example, in some embodiments, control component 34 is configured to use the standard deviation of point by point differences between the potential slow wave and the template by determining the point by point voltage differences between a candidate waveform and the template ($V_{diff}=V_{candidate}-V_{template}$), determining the mean and standard deviation of these differences in units of microvolts, for example ($\mu$=mean ($V_{diff}$), $\sigma$=std ($V_{diff}$)), and validating the candidate waveform based on whether the standard deviation, the standard deviation and the mean, or a product of both breach corresponding thresholds. Theses thresholds may be determined based on information from prior sleep sessions of subject 12 and/or other users, entered and/or selected by a caregiver, subject 12, and/or other users, and/or determined in other ways.

Figure 7:
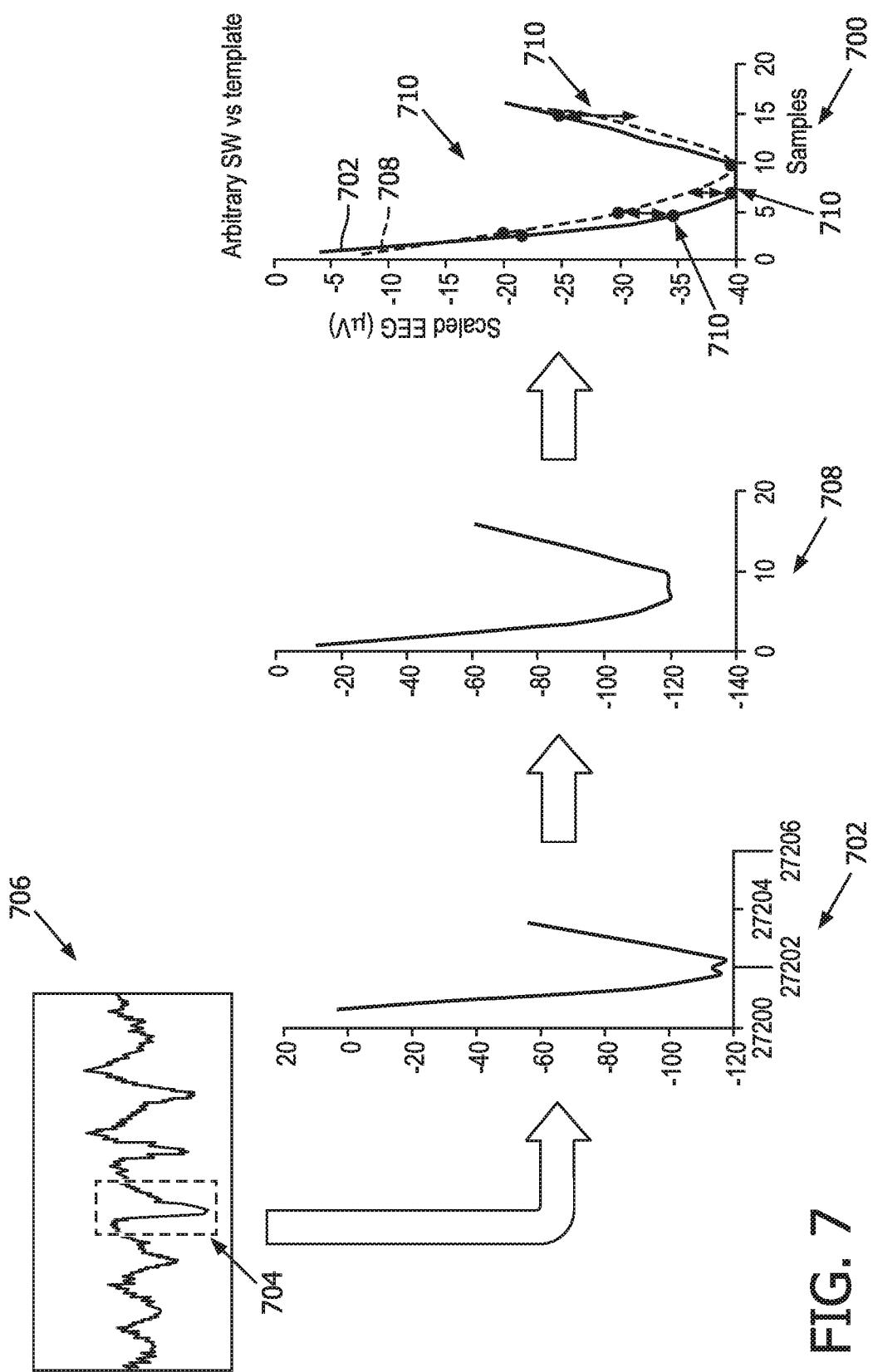
FIG. 7 illustrates a comparison of a candidate slow wave waveform from a portion of an EEG to a template, in accordance with one or more embodiments.

FIG. 7 illustrates comparison 700 of a candidate slow wave waveform 702 from a portion 704 of an EEG 706 (e.g., determined by information component 30 based on information from sensors 13 and 14 shown in FIG. 1) to a template 708. Control component 34 (FIG. 1) is configured to use the mean or the standard deviation of point by point voltage differences 710 between the potential slow wave 702 and the template 708 by determining the point by point voltage differences 710 between candidate waveform 702, and template 708, determining the mean and standard deviation of these differences 710 in units of microvolts, for example, and validating candidate waveform 702 based on whether the mean, the standard deviation, the standard deviation and the mean, or a product of both breach corresponding thresholds.

Returning to FIG. 1, as described above, modulation component 36 is configured to cause sensory stimulator 16 to modulate a timing and/or intensity of the sensory stimulation (e.g., 418 in FIG. 4). Modulation component 36 is configured to cause sensory stimulator 16 to modulate the timing and/or intensity of the sensory stimulation based on the one or more brain activity parameters, values output from the convolutional and/or recurrent layers of the trained neural network, and/or other information. As an example, the volume of auditory stimulation provided to subject 12 may be adjusted and/or otherwise controlled (e.g., modulated) based on value outputs from the deep neural network such as convolutional layer value outputs and recurrent layer value outputs (e.g., sleep stage (soft) prediction probabilities).

In some embodiments, modulation component 36 is configured such that dynamic stimulation intensity (e.g., volume) is provided based on a high-frequency/low-frequency spectral ratio determined based on the frontal EEG signal (e.g., the information in the output signals from sensors 13 and 14 and/or an EEG determined by information component 30). The ratio between high and low frequencies in the EEG reflects sleep depth (SD, see equation below), as lower values correspond to shallow sleep and higher values to deeper sleep.

$$\text{Sleep Depth } (SD) = \log 2\left(\frac{\text{Delta}}{\text{Beta}}\right) + \log 2\left(\frac{\text{Delta}}{\text{Alpha}}\right)$$

Modulation component 36 is configured such that, to minimize the likelihood of disturbing sleep, the intensity (e.g., volume) of the sensory stimulation is modulated according to a linear function, mapping lower volumes to lower sleep depth and higher volumes to higher sleep depth. As a non-limiting example, for auditory stimulation, the volume may be modulated between 35 and 60 dB, where the softest volume is delivered by sensory stimulator 16 (controlled by modulation component 36) when subject 12 is at a minimum sleep depth, and the loudest volume is delivered when subject 12 is at a maximum sleep depth. Modulation component 36 may be configured such that no tones are played if sleep depth breaches a minimum sleep depth threshold, and such that the volume of auditory stimulation does not exceed a predetermined maximum, no matter how deep the sleep depth. Subject 12 specific volume levels may also be used.

In some embodiments, modulation component 36 is configured such that a sleep depth range for stimulation intensity (e.g., volume) titration is determined based on a distribution of sleep depth values within detected N3 sleep (e.g., determined as described above) for sleep depth information for prior sleep sessions of subject 12 and/or other users. In some embodiments, modulation component 36 is configured such that the sleep depth minimum is defined as the sleep depth corresponding to the 35th percentile of a distribution of sleep depth values from the sleep depth information for prior sleep sessions of subject 12 and/or other users. Similarly, a sleep depth maximum may be defined as the sleep depth corresponding to the 98th percentile. These percentiles are not intended to be limiting. They may be any percentile value that allows system 10 to function as described herein.

In some embodiments, modulation component 36 is configured to cause sensory stimulator 16 to modulate the intensity (e.g., volume) of the stimulation using neural network intermediate outputs. The neural network intermediate outputs may include, for example, the soft-outputs (e.g., probabilities for each sleep stage), the convolution outputs, and/or other intermediate outputs. For example, the soft-outputs are continuously varying values that characterize the certainty with which the network detects a given sleep stage. The soft-outputs when N3 is detected can be used to modulate the volume of the stimulation such that the higher the probability of N3 sleep, the louder the volume of the stimulation.

In some embodiments, modulation component 36 is configured to utilize neural network convolutional layer outputs to modulate stimulation delivered to subject 12. In some embodiments, the neural network convolutional outputs may be used instead of the probability values and/or other parameters (e.g., determined directly from the EEG) described above to modulate the stimulation. In some embodiments, the neural network convolutional outputs may be used in addition to the probability values and/or other parameters (e.g., determined directly from the EEG) described above to modulate the stimulation.

In some embodiments, modulation component 36 is configured such that individual convolutional layer outputs are used as a basis for modulating the timing and intensity of the stimulation. In some embodiments, modulation component 36 is configured such that a plurality of convolutional layer outputs facilitate modulating the timing and intensity (e.g., volume) of the stimulation. In some embodiments, the output from the one or more convolutional layers comprises two or more individual outputs from two or more corresponding convolutional layers. In some embodiments, modulation component 36 is configured to determine a ratio of output from one convolutional layer to output from another convolutional layer. In some embodiments, modulation component 36 is configured to cause the one or more sensory stimulators to modulate the timing and/or intensity of the sensory stimulation based on the ratio.

Figure 8:
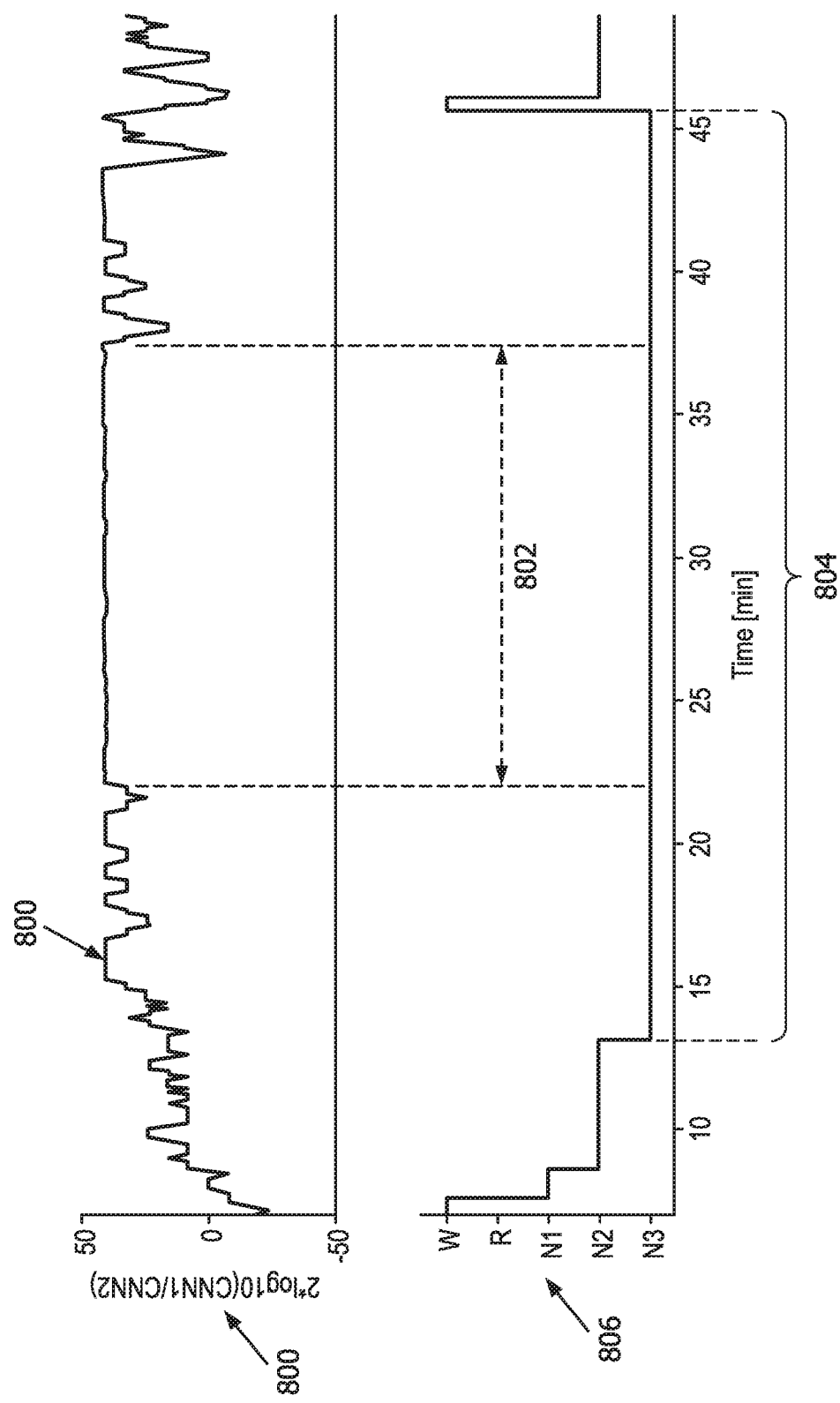
FIG. 8 illustrates a spectral response associated with convolution outputs of a deep neural network, in accordance with one or more embodiments.

By way of a non-limiting example, a spectral response associated with the convolution outputs is shown in FIG. 8. A first output convolutional layer output (CNN1) selectively responds to spectral content in the delta frequency band and a second convolutional layer output (CNN2) selectively responds to spectral content in the beta (15-30 Hz) and gamma (>30 Hz) band. Other convolutional layers outputs may selectively respond to other spectral content. In this example, taking the logarithm of the ratio between CNN1 and CNN2 (e.g., 800) shows a distinct period 802 in detected N3 sleep 804 (as shown in hypnogram 806) where the stimulation can be delivered at a higher intensity (e.g., volume).

In some embodiments, modulation component 36 (FIG. 1) is configured such that cues such as the presence of micro-arousals and/or an exit from slow-wave sleep (e.g., a transition from N3 to N2) can be used to automatically label (as examples when an undesired effect was produced after stimulation) and store sequences of the frontal input signals. These sequences can subsequently be used to retrain/recalibrate the stimulation logic (e.g., when an audible stimulation is delivered and at what strength). Similarly, sequences when the desired effect was produced after stimulation can be labeled and stored so that the underlying algorithms described above can be improved with useful frontal input signals.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensors 13 and 14, sensory stimulator 16, external resources 18, processor 20, and/or other components of system 10. For example, a hypnogram, EEG data, sleep stage probability, and/or other information may be displayed for subject 12 or other users via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 9:
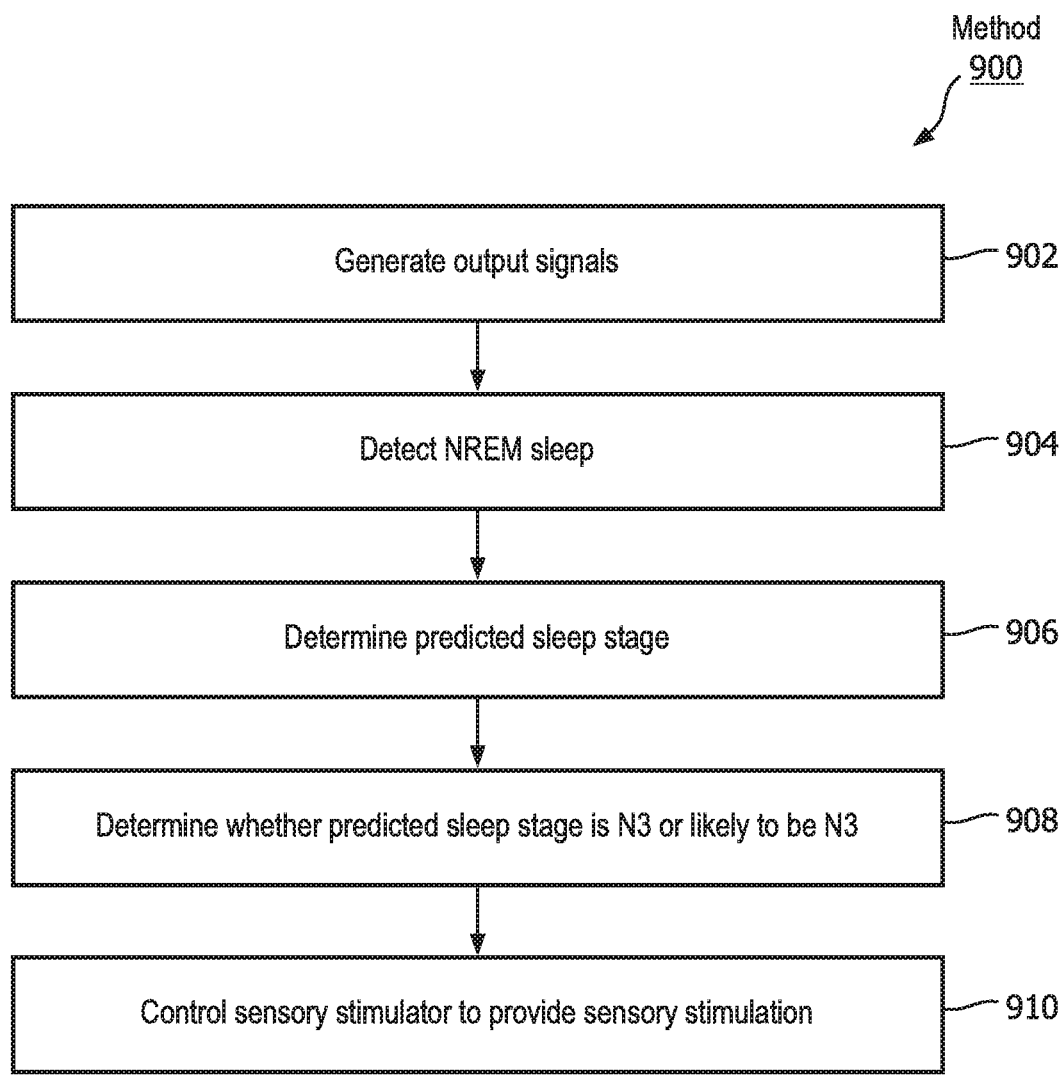
FIG. 9 illustrates method for enhancing NREM sleep by delivering sensory stimulation to a subject during a sleep session with an enhancement system, in accordance with one or more embodiments.

FIG. 9 illustrates method 900 for enhancing NREM sleep by delivering sensory stimulation to a subject during a sleep session with an enhancement system. The system comprises one or more sensors, one or more sensory stimulators, one or more hardware processors configured by machine-readable instructions, and/or other components. The one or more hardware processors are configured to execute computer program components. The computer program components comprise an information component, a model component, a control component, a modulation component, and/or other components. The operations of method 900 presented below are intended to be illustrative. In some embodiments, method 900 may be accomplished with one or more additional operations not described, and/or without one or more of the operations discussed. Additionally, the order in which the operations of method 900 are illustrated in FIG. 9 and described below is not intended to be limiting.

In some embodiments, method 900 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, output signals conveying information related to brain activity of a subject are generated. The output signals are generated during a sleep session of the subject and/or at other times. The output signals are generated with first and second sensors configured to engage a forehead of the subject. In some embodiments, the first sensor comprises a mid-frontal (FPz) electrode, and the second sensor comprises a right ocular electrode (EOGR) or a left ocular electrode (EOGL). In some embodiments, either the first sensor or the second sensor is a reference electrode. In some embodiments, operation 902 is performed by sensors the same as or similar to sensors 13 and 14 (shown in FIG. 1 and described herein).

At an operation 904, NREM sleep is detected in the subject. The NREM sleep is detected in the subject during the sleep session based on the output signals from the first and second sensors and/or based on other information. Operation 904 includes obtaining historical sleep depth information for a population of users. The historical sleep depth information being related to brain activity of the population of users that indicates sleep depth over time during sleep sessions of the population of users. Operation 904 includes causing a neural network to be trained based on the historical sleep depth information by providing the historical sleep depth information as input to the neural network. Operation 904 includes causing, based on the output signals from the first and second sensors, the trained neural network to predict future times during the sleep session at which the subject will be in a deep sleep stage. The trained neural network comprises an input layer, an output layer, and one or more intermediate layers between the input layer and the output layer. In some embodiments, operation 904 is performed by processor components the same as or similar to model component 32 and/or control component 34 (shown in FIG. 1 and described herein).

At an operation 906, a predicted sleep stage is determined. In some embodiments, operation 906 may be a part of operation 904, for example. Operation 906 includes determining, with respect to each of the future times, a predicted sleep stage generated by the output layer of the trained neural network, and sleep stage probability values generated by the one or more intermediate layers of the trained neural network. In some embodiments, operation 906 is performed by a processor component the same as or similar to model component 32 (shown in FIG. 1 and described herein).

At an operation 908, a determination of whether the predicted sleep stage is, or is likely to be N3, is made. In some embodiments, operation 908 may be a part of operation 904, for example. Operation 908 includes, (1) determining that the predicted sleep stage is N3, or (2) determining that the predicted sleep stage is N2, with a ratio of a probability of N3 sleep to a probability of N2 sleep being at least 0.5, and responsive to the predicted sleep stage being N2, with the ratio of the probability of N3 sleep to the probability of N2 sleep being at least 0.5, determining that the N2 sleep is really likely N3 sleep. In some embodiments, operation 908 is performed by processor components the same as or similar to model component 32 and/or control component 34 (shown in FIG. 1 and described herein).

At an operation 910, the sensory stimulator is controlled to provide sensory stimulation to the subject. The sensory stimulation is provided to the subject during the NREM sleep to enhance the NREM sleep in the subject during the sleep session. Operation 910 includes causing, with the one or more hardware processors, the one or more sensory stimulators to provide the sensory stimulation to the subject at the future times and to modulate a timing and/or intensity of the sensory stimulation during the sleep session based on the one or more probability values generated by the one or more intermediate layers.

Operation 910 includes detecting sleep micro-arousals based on the information in the output signals from the first and second sensors and/or other information, and controlling, based on the detected sleep micro-arousals, the one or more sensory stimulators to provide the sensory stimulation to the subject during N3 sleep to enhance the N3 sleep in the subject during the sleep session. A sleep micro-arousal is detected responsive to a breach of a threshold on a power in a power band of an EEG, or based on an additional output from the trained neural network.

Operation 910 includes detecting slow waves based on the information in the output signals from the first and second sensors and/or other information, and controlling, based on the detected slow waves, the one or more sensory stimulators to provide the sensory stimulation to the subject during N3 sleep to enhance the N3 sleep in the subject during the sleep session. A slow wave is detected responsive to a breach of a slow wave minimum peak threshold on a negative going electroencephalogram (EEG) signal, responsive to a breach of a slow wave minimum peak threshold on a filtered negative going EEG signal, wherein the filtering boosts a delta portion of the negative going EEG signal, or based on a comparison of a shape of the filtered negative going EEG signal to a shape of a corresponding slow wave template.

In some embodiments, the one or more intermediate layers of the trained neural network are configured to generate additional values from two or more corresponding convolutional layers. In some embodiments, operation 910 includes determining a ratio of a value from one convolutional layer to a value from another convolutional layer, and causing the one or more sensory stimulators to modulate the timing and/or intensity of the sensory stimulation based on the ratio. In some embodiments, operation 910 is performed by processor components the same as or similar to model component 32, control component 34, and/or modulation component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to enhance non-rapid eye movement (NREM) sleep by delivering sensory stimulation to a subject during a sleep session, the system comprising:
    first and second sensors configured to generate output signals conveying information related to brain activity of the subject during the sleep session, the first and second sensors configured to engage a forehead of the subject;
    one or more sensory stimulators configured to provide the sensory stimulation to the subject during the sleep session; and
    one or more hardware processors coupled to the first and second sensors and the one or more sensory stimulators, the one or more hardware processors configured by machine-readable instructions to:
        detect NREM sleep in the subject during the sleep session based on the output signals from the first and second sensors, and
        control the one or more sensory stimulators to provide the sensory stimulation to the subject during the NREM sleep to enhance the NREM sleep in the subject during the sleep session;
    wherein the one or more hardware processors are further configured by machine-readable instructions to:
        obtain historical sleep depth information for a population of users, the historical sleep depth information being related to brain activity of the population of users that indicates sleep depth over time during sleep sessions of the population of users;
        cause a neural network to be trained based on the historical sleep depth information by providing the historical sleep depth information as input to the neural network;
        cause, based on the output signals from the first and second sensors, the trained neural network to predict future times during the sleep session at which the subject will be in a deep sleep stage, the trained neural network comprising an input layer, an output layer, and one or more intermediate layers between the input layer and the output layer;
        determine, with respect to each of the future times: (i) a predicted sleep stage, the predicted sleep stage generated by the output layer of the trained neural network, and (ii) sleep stage probability values, the sleep stage probability values being generated by the one or more intermediate layers of the trained neural network; and
        responsive to the predicted sleep stage being N3, or the predicted sleep stage being N2 with a ratio of a probability of N3 sleep to a probability of N2 sleep being at least 0.5, cause the one or more sensory stimulators to provide the sensory stimulation to the subject at the future times and to modulate a timing and/or intensity of the sensory stimulation during the sleep session based on the sleep stage probability values generated by the one or more intermediate layers.

2. The system of claim 1, wherein the first and second sensors are configured to engage the forehead of the subject at a distance of less than or equal to 10 centimeters from each other.

3. The system of claim 1, wherein the first sensor comprises a mid-frontal (FPz) electrode, and the second sensor comprises a right ocular electrode (EOGR) or a left ocular electrode (EOGL).

4. The system of claim 1, wherein either the first sensor or the second sensor is a reference electrode.

5. The system of claim 1, wherein the one or more hardware processors are further configured by machine-readable instructions to detect sleep micro-arousals based on the information in the output signals from the first and second sensors, and control, based on the detected sleep micro-arousals, the one or more sensory stimulators to provide the sensory stimulation to the subject during N3 sleep to enhance the N3 sleep in the subject during the sleep session, wherein a sleep micro-arousal is detected:
    responsive to a breach of a threshold on a power in a power band of an electroencephalogram (EEG), or
    based on an additional output from the trained neural network.

6. The system of claim 1, wherein the one or more hardware processors are further configured by machine-readable instructions to detect slow waves based on the information in the output signals from the first and second sensors, and control, based on the detected slow waves, the one or more sensory stimulators to provide the sensory stimulation to the subject during N3 sleep to enhance the N3 sleep in the subject during the sleep session, wherein a slow wave is detected:
    responsive to a breach of a slow wave minimum peak threshold on a negative going electroencephalogram (EEG) signal,
    responsive to a breach of a slow wave minimum peak threshold on a filtered negative going EEG signal, wherein the filtering boosts a delta portion of the negative going EEG signal, or
    based on a comparison of a shape of the filtered negative going EEG signal to a shape of a corresponding slow wave template.

7. The system of claim 1, wherein the one or more hardware processors are further configured by machine-readable instructions:

such that the one or more intermediate layers of the trained neural network are configured to generate additional values from two or more corresponding convolutional layers;
to determine a convolutional layer ratio of a value from one convolutional layer to a value from another convolutional layer, and
to cause the one or more sensory stimulators to modulate the timing and/or intensity of the sensory stimulation based on the convolutional layer ratio.

8. A method for enhancing non-rapid eye movement (NREM) sleep by delivering sensory stimulation to a subject during a sleep session with an enhancement system, the system comprising first and second sensors, one or more sensory stimulators, and one or more hardware processors coupled to the first and second sensors and the one or more sensory stimulators, the method comprising:
generating, with the first and second sensors, output signals conveying information related to brain activity of the subject during the sleep session, the first and second sensors configured to engage a forehead of the subject;
detecting, with the one or more hardware processors, NREM sleep in the subject during the sleep session based on the output signals from the first and second sensors;
controlling, with the one or more processors, the one or more sensory stimulators to provide the sensory stimulation to the subject during the NREM sleep to enhance the NREM sleep in the subject during the sleep session;
obtaining, with the one or more hardware processors, historical sleep depth information for a population of users, the historical sleep depth information being related to brain activity of the population of users that indicates sleep depth over time during sleep sessions of the population of users;
causing, with the one or more hardware processors, a neural network to be trained based on the historical sleep depth information by providing the historical sleep depth information as input to the neural network;
causing, with the one or more hardware processors, based on the output signals from the first and second sensors, the trained neural network to predict future times during the sleep session at which the subject will be in a deep sleep stage, the trained neural network comprising an input layer, an output layer, and one or more intermediate layers between the input layer and the output layer;
determining, with the one or more hardware processors, with respect to each of the future times: (i) a predicted sleep stage, the predicted sleep stage being generated by the output layer of the trained neural network, and (ii) sleep stage probability values, the sleep stage probability values being generated by the one or more intermediate layers of the trained neural network; and
responsive to the predicted sleep stage being N3, or the predicted sleep stage being N2 with a ratio of a probability of N3 sleep to a probability of N2 sleep being at least 0.5, causing, with the one or more hardware processors, the one or more sensory stimulators to provide the sensory stimulation to the subject at the future times and to modulate a timing and/or intensity of the sensory stimulation during the sleep session based on the sleep stage probability values generated by the one or more intermediate layers.

9. The method of claim 8, wherein the first sensor comprises a mid-frontal (FPz) electrode, and the second sensor comprises a right ocular electrode (EOGR) or a left ocular electrode (EOGL).

10. The method of claim 8, wherein either the first sensor or the second sensor is a reference electrode.

11. The method of claim 8, further comprising detecting, with the one or more hardware processors, sleep micro-arousals based on the information in the output signals from the first and second sensors, and controlling, with the one or more hardware processors, based on the detected sleep micro-arousals, the one or more sensory stimulators to provide the sensory stimulation to the subject during N3 sleep to enhance the N3 sleep in the subject during the sleep session, wherein a sleep micro-arousal is detected:
responsive to a breach of a threshold on a power in a power band of an electroencephalogram (EEG), or based on an additional output from the trained neural network.

12. The method of claim 8, further comprising detecting, with the one or more hardware processors, slow waves based on the information in the output signals from the first and second sensors, and controlling, with the one or more hardware processors, based on the detected slow waves, the one or more sensory stimulators to provide the sensory stimulation to the subject during N3 sleep to enhance the N3 sleep in the subject during the sleep session, wherein a slow wave is detected:
responsive to a breach of a slow wave minimum peak threshold on a negative going electroencephalogram (EEG) signal,
responsive to a breach of a slow wave minimum peak threshold on a filtered negative going EEG signal, wherein the filtering boosts a delta portion of the negative going EEG signal, or
based on a comparison of a shape of the filtered negative going EEG signal to a shape of a corresponding slow wave template.

13. The method of claim 8, wherein:
the one or more intermediate layers of the trained neural network are configured to generate additional values from two or more corresponding convolutional layers;
the method further comprises determining, with the one or more hardware processors, a convolutional layer ratio of a value from one convolutional layer to a value from another convolutional layer, and
the method further comprises causing, with the one or more hardware processors, the one or more sensory stimulators to modulate the timing and/or intensity of the sensory stimulation based on the convolutional layer ratio.

* * * * *